United States Patent
Duan et al.

(10) Patent No.: US 12,377,288 B2
(45) Date of Patent: Aug. 5, 2025

(54) EVALUATION AND PRESENTATION OF ROBUSTNESS OF A TREATMENT PLAN

(71) Applicant: Elekta (Shanghai) Technology Co., Ltd., Shanghai (CN)

(72) Inventors: Weisheng Duan, Shanghai (CN); Yue Yuan, Shanghai (CN)

(73) Assignee: Elekta (Shanghai) Technology Co., Ltd., Shanghai (CN)

( * ) Notice: Subject to any disclaimer, the term of this patent is extended or adjusted under 35 U.S.C. 154(b) by 170 days.

(21) Appl. No.: 18/031,302

(22) PCT Filed: Oct. 12, 2020

(86) PCT No.: PCT/CN2020/120355
§ 371 (c)(1),
(2) Date: Apr. 11, 2023

(87) PCT Pub. No.: WO2022/077160
PCT Pub. Date: Apr. 21, 2022

(65) Prior Publication Data
US 2023/0372736 A1 Nov. 23, 2023

(51) Int. Cl.
*A61N 5/10* (2006.01)
*G16H 20/40* (2018.01)

(52) U.S. Cl.
CPC .......... *A61N 5/1031* (2013.01); *G16H 20/40* (2018.01); *A61N 2005/1087* (2013.01)

(58) Field of Classification Search
CPC .......... A61N 5/1031; A61N 2005/1087; A61N 5/1071; A61N 5/103; G16H 20/40
See application file for complete search history.

(56) References Cited

U.S. PATENT DOCUMENTS

| 2013/0197878 A1* | 8/2013 | Fiege | G06F 30/20 703/2 |
| 2014/0018602 A1 | 1/2014 | Nord et al. | |

(Continued)

FOREIGN PATENT DOCUMENTS

| CN | 106730412 A | 5/2017 |
| CN | 110289631 | 9/2019 |

(Continued)

OTHER PUBLICATIONS

"European Application Serial No. 20956942.5, Response filed Oct. 27, 2023 to Communication pursuant to Rules 161(2) and 162 EPC mailed May 31, 2023", 8 pgs.

(Continued)

*Primary Examiner* — Kiho Kim
(74) *Attorney, Agent, or Firm* — Schwegman Lundberg & Woessner, P.A.

(57) ABSTRACT

Systems and methods for evaluating and presenting robustness of a radiotherapy treatment plan for use in radiotherapy are discussed. An exemplary system includes a processor to generate, in a radiation simulation in accordance with the treatment plan under evaluation, dose distributions at an anatomical structure under a nominal condition and one or more artificially imposed uncertainty conditions, determine a dose distribution characteristic for the anatomical structure using the received dose distributions, and generate a robustness indicator of the treatment plan. The dose distributions may be determined at a target structure and one or more structures at risk, and presented graphically in a three-dimensional dose-volume-structure space. An output circuit can output the dose distribution characteristic or the robustness indicator to a user or a treatment planning system.

24 Claims, 13 Drawing Sheets

(56) References Cited

U.S. PATENT DOCUMENTS

| | | |
|---|---|---|
| 2014/0114114 A1 | 4/2014 | Brown |
| 2015/0095043 A1 | 4/2015 | Cordero Marcos et al. |
| 2017/0014642 A1 | 1/2017 | An et al. |
| 2020/0121953 A1 | 4/2020 | Fredriksson |
| 2020/0298019 A1 | 9/2020 | Isola et al. |

FOREIGN PATENT DOCUMENTS

| | | |
|---|---|---|
| CN | 110869086 | 3/2020 |
| CN | 111542371 | 8/2020 |
| CN | 116507388 | 7/2023 |
| CN | 116507388 B | 10/2024 |
| CN | 119280707 A | 1/2025 |
| JP | 2018187089 A | 11/2018 |
| WO | WO-2022077160 A1 | 4/2022 |

OTHER PUBLICATIONS

"Chinese Application Serial No. 202080106067.7, Office Action mailed Apr. 19, 2024", W English Translation, 18 pgs.

"Chinese Application Serial No. 202080106067.7, Response filed Jun. 17, 2024 to Office Action mailed Apr. 19, 2024", W English Claims, 17 pgs.

"International Application Serial No. PCT/CN2020/120355, International Search Report mailed Jul. 9, 2021", 4 pgs.

"International Application Serial No. PCT/CN2020/120355, Written Opinion mailed Jul. 9, 2021", 5 pgs.

"European Application Serial No. 20956942.5, Extended European Search Report mailed Jun. 14, 2024", 7 pgs.

"European Application Serial No. 20956942.5, Response filed Jan. 2, 2025 to Extended European Search Report mailed Jun. 14, 2024", 17 pgs.

Biston, M-C, et al., "Time of PTV is ending, robust optimization comes next", Cancer Radiotherapie, Elsevier, Paris, Fr, vol. 24, No. 6, (Aug. 26, 2020), 676-686.

Hernandez, Victor, et al., "What is plan quality in radiotherapy? The importance of evaluating dose metrics, complexity, and robustness of treatment plans", Radiotherapy And Oncology, Elsevier, Ireland, vol. 153, (Sep. 25, 2020), 26-33.

* cited by examiner

EVALUATION AND PRESENTATION OF ROBUSTNESS OF A TREATMENT PLAN

PRIORITY APPLICATIONS

This application is a U.S. National Stage Filing under 35 U.S.C. § 371 from International Application No. PCT/CN2020/120355, filed on Oct. 12, 2020, and published as WO2022/077160 on Apr. 21, 2022; the benefit of priority of which is hereby claimed herein, and which application and publication are hereby incorporated herein by reference in its entirety.

TECHNICAL FIELD

This document relates generally to dose calculation in a radiation therapy treatment system, and more particularly, to systems and methods for evaluating robustness of a radiotherapy treatment plan.

BACKGROUND

Radiation therapy (or "radiotherapy") has been used to treat cancers or other ailments in mammalian tissue. One such radiotherapy technique is provided using a linear accelerator (also referred to as "linac"), whereby a targeted region is irradiated by high-energy particles (e.g., electrons, high-energy photons, and the like). MR-linac is a radiation treatment system that combines linac radiotherapy with diagnostic-level magnetic resonance imaging (MRI). In another example, radiotherapy may be provided using a heavy charged particle accelerator (e.g. protons, carbon ions, and the like). The goal of radiation therapy is to maximize radiation dose to target tissue (e.g., tumor or other abnormal tissue) while minimizing damage to the surrounding healthy tissue, such as "organ(s) at risk" (OARs). A physician prescribes a predefined amount of radiation dose to the target (tumor or other abnormal tissue) and clinical dose constraints for surrounding organs similar to a prescription for medicine. Generally, ionizing radiation in the form of a collimated beam is directed from an external radiation source toward a patient. The radiation beam can be accurately controlled to ensure the dose delivery.

A specified or selectable beam energy can be used for delivering a diagnostic energy level range or a therapeutic energy level range. Ionizing radiation in the form of a collimated beam may be directed from an external radiation source toward a patient. Modulation of a radiation beam may be provided by one or more attenuators or collimators, such as a multi-leaf collimator (MLC) and jaws. The intensity and shape of the radiation beam can be adjusted by collimators to avoid damaging healthy tissue adjacent to the targeted tissue, such as by conforming the projected beam to a profile of the targeted tissue.

Treatment planning is a process involving determination of radiotherapy parameters for implementing a treatment goal under the constraints. Examples of the radiotherapy parameters include radiation beam angles, dose intensity level, dose distribution, etc. The radiation dose can be calculated using a dose calculation algorithm. The outcome of the treatment planning process is a radiotherapy treatment plan (also referred to as a "treatment plan" or simply a "plan"). The treatment plan can be developed using a treatment planning system (TPS). A treatment plan is custom designed for each patient before radiotherapy delivery can be delivered to a patient. In order to create a plan, one or more medical imaging techniques, such as images from X-rays, computed tomography (CT), nuclear magnetic resonance (MR), positron emission tomography (PET), single-photon emission computed tomography (SPECT), or ultrasound must be used to provide images of a target tumor.

Ideally, dose determined from a treatment plan should equal to the dose received by the patient. However, uncertainties in treatment planning may cause deviations of the delivered dose from the calculated dose. The treatment uncertainty may come from different sources. The quality of a radiation treatment plan is strongly dependent upon the robustness of the treatment plan to various sources of uncertainties. Careful evaluation of plan robustness can be helpful in optimizing treatment plan design prior to delivery.

Overview

The design of a treatment plan may include using images of patient anatomy to identify a target structure (e.g., a target tumor) and surrounding tissue near the target structure (e.g., OARs), delineate the target that is to receive prescribed radiation dose, and similarly delineate nearby tissue such as OARs of damage from the radiation treatment. A treatment plan may be developed using a software noted as treatment planning system (TPS). For example, an automated tool (e.g., ABAS® provided by Elekta AB, Sweden) may be used to assist in identifying or delineating the target tumor and organs at risk. The treatment plan may then be created using an optimization technique based on clinical and dosimetric objectives and constraints (e.g., maximum, minimum, or mean radiation doses to the tumor and the OARs).

Therapeutic ratio is an important consideration in treatment plan design, which represents a balance between the probability of target control and complications or damages to nearby normal tissue, such as OARs. The therapeutic ratio may be affected by a radiation dose distribution across the target and nearby tissue. When designing a treatment plan, a planner tries to comply with various treatment objectives or constraints, and taking into account their individual importance to produce a clinically acceptable treatment plan. The treatment plan may include parameters specifying the direction, cross-sectional shape, and intensity of one or more radiation beams. In some examples, a treatment plan may include dose "fractioning," whereby a sequence of radiation treatments may be provided over a predetermined period of time (e.g., 30-45 daily fractions), with each treatment including a specified fraction of a total prescribed dose. Once generated, the treatment plan can be executed by positioning the patient in the treatment machine and delivering the prescribed radiation therapy directed by the optimized plan parameters.

Radiation therapy may be provided by using particles such as protons, also known as proton therapy. Compared to other forms of radiation therapy (e.g., X-ray), proton therapy can advantageously improve the therapeutic ratio, provide superior dose distribution with minimal exit dose, and at least in some patients have less complications or side effects to the normal tissues such as OARs than other forms of radiation such as X-ray. The radiation dose can be increased for tumors that require high radiation doses to achieve desired local control. As such, patient quality of life during and after proton therapy treatment may be improved.

Different options exist to design proton therapy treatments. In an example, a proton beam is used to deliver a uniform dose to the target. In another example, multiple beams may be used, each delivering a uniform dose to a different part of the target. Such an approach more flexibility to spare organs at risk, particularly if the target is partially wrapped around such an organ. In some examples, each beam can deliver an optimized inhomogeneous dose distribution to the target, which is a technique known as intensity modulated proton therapy. The dose delivered by all beams combined then yields the desired uniform dose.

The finite ranges of the proton beam need to be accurately determined in designing a proton treatment plan. The range is defined at the position where the dose has decreased to a certain percentage (e.g., 80%, or 90%) of the maximum dose, such as in the distal dose falloff. For this purpose, proton stopping powers may be determined for the patient's anatomy. A conversion algorithm is used to determine the stopping powers from a CT scan, considering the typical composition of human tissues. The range of the proton beam is normally different throughout the treatment field. In the case of a uniform dose, the beam is given a range at each position that is sufficient to reach the distal surface of the target volume. Intensity modulated beams may also stop within the target volume. Unlike beams that traverse homogeneous matter, these ranges cannot always be clearly defined as a single mean range. If the anatomy is inhomogeneous, protons that enter the patient with the same energy and at the same position may end up having different ranges, because differences in the scattering can result in different trajectories through the anatomy.

A challenge in proton therapy is the uncertainty in the range of the proton beam. The end-of-range is where the beam features its sharpest dose gradient. Therefore, an undershoot of the proton range can lead to the distal edge of the tumor not receiving the intended dose. Sources of uncertainties in the proton range may include systematic uncertainties and random uncertainties. Systematic uncertainties may affect most of the tissue traversed by a typical beam, and impact the entire course of treatment. Random uncertainties can be attributed to the reproducibility of the beam and the patient setup. Examples of the sources of uncertainties may include, for example, CT Hounsfield unit (HU) of stopping power conversion uncertainties (which may be related to patient size, scanning techniques, or reconstruction algorithms), stopping power measurement or calculation uncertainties, CT artifacts, uncertainties in the formation of proton beams, uncertainties in the determination of radiological thickness of bolus/compensator materials and accessories, interfractional patient setup error such as due to differences between a patient's position and location at treatment compared to that at treatment simulation and difference between fractions, errors in reproducing a patient's position, organ motion, and anatomical changes (e.g., tumor regression or growth during treatment course), among others.

Radiotherapy such as proton therapy is based on a carefully designed treatment plan for the individual patient. For the treatment plan, a CT scan is obtained with the patient in the same position as used during treatment. Based on the prescription of the physician, a treatment planning system is then used to design proton beams that together deliver a dose distribution that provides a good trade-off between target coverage and sparing of organs at risk. For the target, the goal is typically to create a high and uniform dose volume. In the case of OARs, the dose tolerance and the importance of the mean dose or the maximum dose varies depending on the type of organ.

A treatment plan needs to be robust to range uncertainties including systematic and random inter-fractional patient setup errors to ensure that the target volume receives a tumoricidal dose, and that the OAR doses are kept below complication thresholds. Robustness evaluation of a treatment plan against setup and range uncertainties can be helpful in a treatment planning process, and may influence clinical decision making. To evaluate a treatment plan, dose distributions may be calculated, in accordance with the treatment plan being evaluated, respectively under a nominal condition and one or more uncertainty conditions deviating from the nominal condition. Such dose distributions may be calculated respectively for the target structure and surrounding tissue (e.g., one or more OARs). A clinical user can then determine the quality and robustness of the treatment plan based on the dose distributions of the target and/or the dose distributions of the surrounding tissue.

Dose distributions may be represented by dose-volume histograms (DVHs). Conventionally, dose distributions under different conditions (e.g., nominal and uncertainty conditions) for different structures (e.g., the target and OARs) are graphically presented on one two-dimensional (2D) DVH graph. Reviewing and interpreting the dose distributions from such a DVH graph can be challenging, because often times the DVHs of one structure may overlap with the DVHs of another structure, making it difficult to distinguish the dose distributions between different structures. Additionally, for a particular structure, the overlay of a cluster of DVHs for different scenarios (e.g., nominal and uncertainty conditions) does not provide easily digestible information about treatment plan robustness, and there are few qualitative or quantitative indicators of robustness. For at least those reasons stated above, the present inventors have recognized an unmet need for improve evaluation of treatment plan robustness and more efficient presentation of such information.

The present document discusses systems and methods for evaluating and presenting robustness of a radiotherapy treatment plan for use in radiotherapy. An exemplary system includes a processor to generate, in a radiation simulation in accordance with the radiotherapy treatment plan under evaluation, dose distributions at an anatomical structure under a nominal condition and one or more artificially imposed uncertainty conditions, determine a dose distribution characteristic for the anatomical structure using the received dose distributions, and generate a robustness indicator of the radiotherapy treatment plan. The dose distributions may be determined at a target structure and one or more structures at risk (e.g., OARs), and presented graphically in a three-dimensional (3D) dose-volume-structure space. An output circuit can output the dose distribution characteristic or the robustness indicator to a user or a treatment planning system.

Various examples discussed herein may improve the process of evaluating and presenting treatment plan robustness to a user. Compared to conventional 2D DVH graph, a 3D DVH graph, as discussed according to various examples in this document, better organizes and presents the information of dose distributions (e.g., DVHs) for different stimulated scenarios (e.g., a nominal condition and a number of artificially imposed uncertainty conditions) at different structures (e.g., target structure and one or more nearby OARs). The DVHs for different structures are spread out along a "structure" axis in the 3D dose-volume-structure space. This may prevent or substantially reduce the chance of overlapping DVHs, thereby allowing a clinical user to more precisely and efficiently identify differences among dose distributions of different structures under different simulated scenarios. According to some examples, the clinical user is provided with graphical control tools to manipulate the 3D DVH graph to improve the viewing experience, control flexibility, and more comprehensive evaluation of treatment plan robustness. The present document further describes various robustness indicators representing, for example, statistical properties of the DVHs, that may be presented on the 3D DVH graph. The robustness indicator provides more concise and meaningful information about robustness of the treatment plan under evaluation. As a result, treatment planning can be done more efficiently, clinician time and effort can be reduced, and enhanced user experience and more precise assessment of plan robustness can be achieved. By implementing the improved treatment plan evaluation process as discussed herein, individualized radiotherapy and patient outcome can be improved, and overall cost saving associated with radiotherapy treatment planning can be achieved.

The above is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various examples discussed in the present document.

DETAILED DESCRIPTION

In the following detailed description, reference is made to the accompanying drawings which form a part hereof, and which is shown by way of illustration-specific examples in which the present disclosure may be practiced. These examples, which are also referred to herein as "examples," are described in sufficient detail to enable those skilled in the art to practice the disclosure, and it is to be understood that the examples may be combined, or that other examples may be utilized and that structural, logical and electrical changes may be made without departing from the scope of the present disclosure. The following detailed description is, therefore, not be taken in a limiting sense, and the scope of the present disclosure is defined by the appended aspects and their equivalents.

Figure 1:
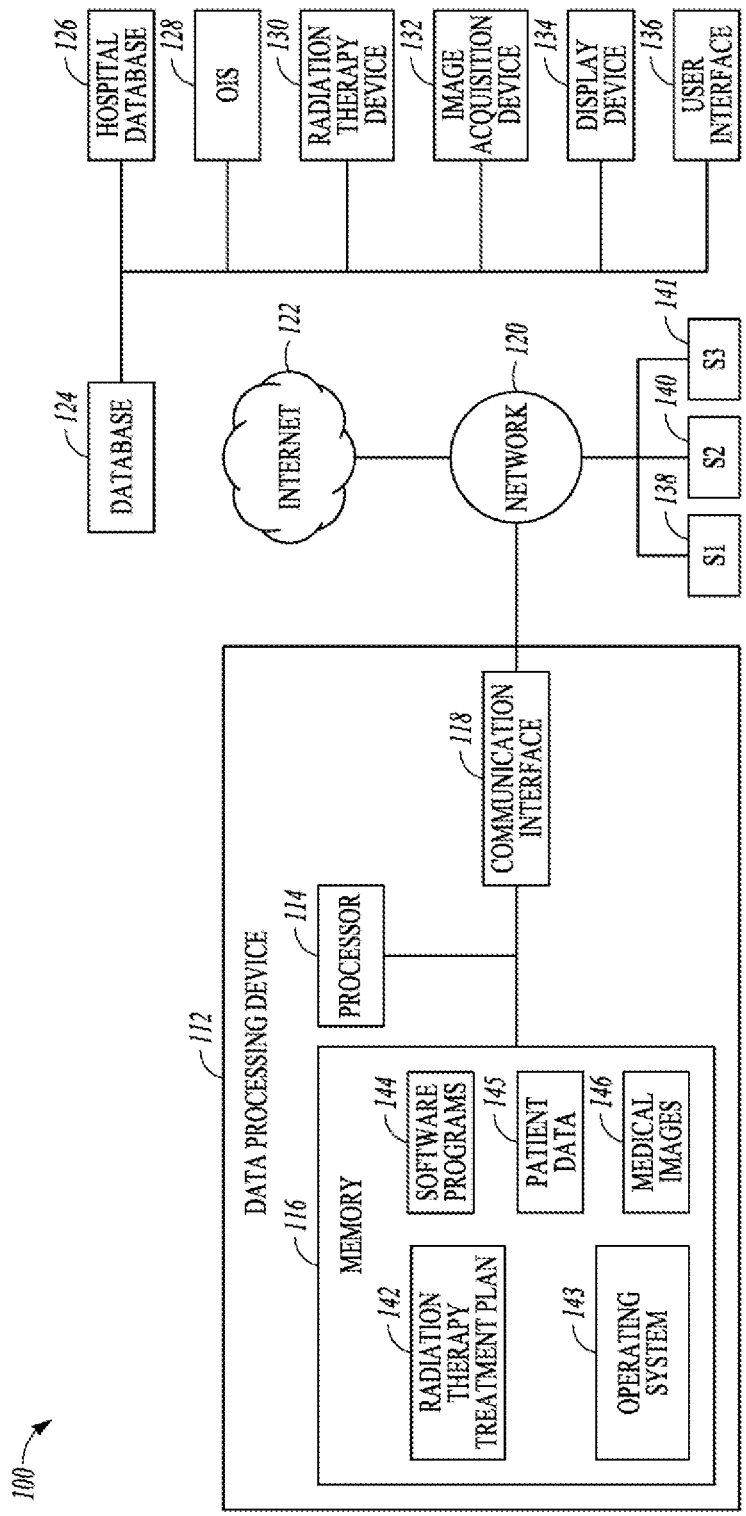
FIG. 1 illustrates an exemplary radiotherapy system.

FIG. 1 illustrates an exemplary radiotherapy system 100 for providing radiation therapy to a patient. The radiotherapy system 100 includes, among other components, a data processing device 112. The data processing device 112 may be connected to a network 120. The network 120 may be connected to the Internet 122. The network 120 can connect the data processing device 112 with one or more of a database 124, a hospital database 126, an oncology information system (OIS) 128, a radiation therapy device 130, an image acquisition device 132, a display device 134, and a user interface 136. The data processing device 112 can be configured to generate radiation therapy treatment plans 142 to be used by the radiation therapy device 130.

The data processing device 112 may include a memory 116, a processor 114, and a communication interface 118. The memory 116 may store computer-executable instructions, such as a radiation therapy treatment plan 142 (e.g., original treatment plans, adapted treatment plans and the like), an operating system 143, software programs 144, and any other computer-executable instructions to be executed by the processor 114. The memory 116 may additionally store data, such as medical images 146, patient data 145, and other data required to implement a radiation therapy treatment plan 142.

The software programs 144 may include one or more software packages that, when executed by a machine such as the processor 114, can perform specific image processing and generating a radiotherapy treatment plan 142. In an example, the software programs 144 can convert medical images of one format (e.g., MRI) to another format (e.g., CT) by producing synthetic images, such as pseudo-CT images. For instance, the software programs 144 may include image processing programs to train a predictive model for converting a medical image from the medical images 146 in one modality (e.g., an MR image) into a synthetic image of a different modality (e.g., a pseudo CT image); alternatively, the trained predictive model may convert a CT image into an MR image. In another example, the software programs 144 may register the patient image (e.g., a CT image or an MR image) with that patient's dose distribution (also represented as an image) so that corresponding image voxels and dose voxels are associated appropriately by the network. In yet another example, the software programs 144 may substitute functions of the patient images such as signed distance functions or processed versions of the images that emphasize some aspect of the image information. Such functions might emphasize edges or differences in voxel textures, or any other structural aspect useful to neural network learning. The software programs 144 may substitute functions of the dose distribution that emphasize some aspect of the dose information. Such functions might emphasize steep gradients around the target or any other structural aspect useful to neural network learning.

In an example, the software programs 144 may generate projection images for a set of two-dimensional (2D) and/or 3D CT or MR images depicting an anatomy (e.g., one or more targets and one or more OARs) representing different views of the anatomy from the treatment gantry angles of the radiotherapy equipment. For example, the software programs 144 may process the set of CT or MR images and create a stack of projection images depicting different views of the anatomy depicted in the CT or MR images from various perspectives of the gantry of the radiotherapy equipment. In particular, one projection image may represent a view of the anatomy from 0 degrees of the gantry, a second projection image may represent a view of the anatomy from 45 degrees of the gantry, and a third projection image may represent a view of the anatomy from 90 degrees of the gantry. The degrees may be directions of the beams relative to a particular axis of the anatomy depicted in the CT or MR images. The axis may remain the same for each beam of the different degrees.

In an example, the software programs 144 may generate graphical aperture image representations of MLC leaf positions at various gantry angles. These graphical aperture images are also referred to as aperture images. In particular, the software programs 144 may receive a set of control points that are used to control a radiotherapy device to produce a shaped radiotherapy beam. The control points may represent the beam intensity, gantry angle relative to the patient position, and the leaf positions of the MLC, among other machine parameters. Based on these control points, a graphical image may be generated to graphically represent the beam shape and intensity that is output by the MLC and jaws at a particular gantry angle. The software programs 144 may align a graphical image of the aperture at a particular gantry angle with the corresponding projection image at that angle that was generated. The images are aligned and scaled with the projections such that the projection image pixel is aligned with the corresponding aperture image pixel.

The software programs 144 may include a treatment planning software. The treatment planning software, when executed such as by a treatment planning system (TPS), can generate the radiation therapy treatment plan 142. In an example, execution of the treatment planning software can produce a graphical aperture image representation of MLC leaf positions at a given gantry angle for a projection image of the anatomy representing the view of the anatomy from the given gantry angle.

As depicted, the software programs 144 may include a beam model. The beam model is represented by various characteristics of radiation beams with the imports of a broad radiation field specific to a treatment machine and exiting the radiation machine and impinging upon the patient. Using an appropriately determined beam model, machine parameters or control points for a given type of machine can be calculated, and the radiation machine can output a beam from the MLC that achieves the same or similar estimated graphical aperture image representation of the MLC leaf positions and intensity. The treatment planning software, when executed, may output an image representing an estimated image of the beam shape and the intensity for a given gantry angle and for a given projection image of the gantry at that angle, and the function may compute the control points for a given radiotherapy device to achieve that beam shape and intensity.

The beam model can be represented by a function of one or more beam model types that characterize various properties of one or more radiation modality, such as a photon or an electron. Different beam models may differ in the number and/or configuration of the radiation sources. As such, beam model parameters (e.g., size, position, energy spectrum, or fluence distribution of a radiation source) may vary from one beam model type to another. By way of example and not limitation, the beam model parameters may include size and position of one or more photon sources within the radiation machine, maximum or average energy of a photon spectrum for photons emitted from the radiation machine, factors describing the shape of a photon spectrum emitted from the radiation machine, size and position of one or more electron sources within the radiation machine, maximum or average energy of an electron spectrum emitted from the radiation machine, factors describing the shape of an electron spectrum, or one or more numbers describing how radiation (e.g., electrons or photons) emitted by the radiation machine can vary off-axis, among others.

In addition to the memory 116 storing the software programs 144, the software programs 144 may additionally or alternatively be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to data processing device 112 may be executed by processor 114.

The processor 114 may be communicatively coupled to the memory 116, and the processor 114 may be configured to execute computer executable instructions stored therein. The processor 114 may send or receive medical images 146 to the memory 116. For example, the processor 114 may receive medical images 146 from the image acquisition device 132 via the communication interface 118 and network 120 to be stored in memory 116. The processor 114 may also send medical images 146 stored in memory 116 via the communication interface 118 to the network 120 be stored in the database 124 or the hospital database 126.

The processor 114 can generate a beam model for a particular radiation machine (with particular collimator type and/or energy level). The generated beam model can be stored in the software programs 144. In an example, the beam model may be presented to a user, such as being displayed on the display device 134. Other information may be presented to the user (e.g., displayed on the display device 134), such as a report containing beam model parameters, geometry information, dose calculation settings, and fitting results that show both measured dose distribution and calculated dose distribution based on the beam model. The fitting results. In an example, the beam model may be delivered to a TPS for clinical treatment planning.

In some examples, before a beam model is deploying to a TPS for clinical use, the processor 114 may validate the beam model after the model is generated. The validation may include importing the beam model into a TPS executing a treatment planning software (e.g., Monaco® treatment planning system, manufactured by Elekta AB of Stockholm, Sweden), and calculating the dose distribution in a virtual phantom (e.g., a water phantom). Algorithms for calculating the dose distribution in the virtual phantom may include a Monte Carlo dose algorithm, such as an XVMC algorithm. The calculated dose distribution can be compared to the measured beam characterization from a target radiation machine (e.g., a linac) to determine if the calculated dose satisfies dosimetric verification criteria, also referred to as delivery criteria, such as one or more dose metrics falling within a tolerance range (±x %) with respect to the measured dose metrics.

The processor 114 may include a dose engine configured to calculate a dose metric or dose statistic using a beam model. Various algorithms may be used to calculate the dose. In an example, the dose engine may use a Monte Carlo algorithm or a Collapsed Cone Convolution (CCC) algorithm (which may be implemented as a software package stored in the software programs 144) to calculate the dose metrics or dose statistics. Examples of the dose engine may include a voxel Monte Carlo (VMC) dose engine, an X-ray voxel Monte Carlo (XV MC) dose engine, or a GPU Monte Carlo Dose (GPUMCD).

The processor 114 may include at least a portion of a treatment planning system (TPS) configured to execute a treatment planning software (as part of the software programs 144), and generate the radiation therapy treatment plan 142 using the beam model, the medical images 146, and patient data 145. The medical images 146 may include information such as imaging data associated with a patient anatomical region, organ, or volume of interest segmentation data. The patient data 145 may include information such as: functional organ modeling data (e.g., serial versus parallel organs, appropriate dose response models, etc.); radiation dosage data (e.g., DVH information); or other clinical information about the patient and treatment (e.g., other surgeries, chemotherapy, previous radiotherapy, etc.).

In some examples, the processor 114 may analyze the robustness of a candidate treatment plan. The processor 114 can calculate dose distributions at one or more anatomical structures in a radiation simulation process using the candidate treatment plan. The dose distributions may be calculated respectively for a target structure to receive radiation treatment, and one or more nearby structures at risk (e.g., OARs) to avoid radiation treatment. For a specific anatomical structure, the dose distributions may be calculated under different simulated scenarios corresponding to, for example, a nominal condition and one or more artificially imposed uncertainty conditions representing respective deviations from the nominal condition. The processor 114 may determine a dose distribution characteristic respectively for each of the anatomical structures (e.g., the target structure or an OAR) using the received dose distributions. In some examples, the dose distributions may be represented by dose-volume histograms (DVHs). The processor 114 may use the DVHs to generate a dose distribution characteristic for an anatomical structure. By way of example and not limitation, and as further discussed below with reference to FIG. 9, the dose distribution characteristic may include boundary DVHs, a DVH range due to uncertainty conditions applied, a DVH band graphically representing the DVH range, an extreme-scenario DVH representing an uncertainty DVH that significantly deviates from the nominal DVH based on a specific dosimetric criterion, identification of out-of-range DVHs falling outside a tolerance margin according to a dosimetric criterion, an out-of-range sub-band graphically representing a range of the out-of-range DVHs, a count of the out-of-range DVHs, or a number (e.g., a percentage) relative to the total number of uncertainty DVHs, among others.

The processor 114 may generate a robustness indicator of the candidate treatment plan based on the dose distribution characteristic. The dose distribution characteristic or the robustness indicator may be stored in the memory 116, and accessible by a user or a treatment planning system. In an example, the dose distribution characteristic or the robustness indicator may be presented to a user, such as being displayed on the display device 134. In an example, a three-dimensional (3D) DVH graph may be generated, and displayed on the display device 134. In some examples, the user interface 136 may include one or more user controls (e.g., on-screen control elements, or a touch screen that enables finger touch and navigation control) that enable a user to manipulate the display of the DVH graph to more effectively reveal the differences of the dose distribution characteristics between different structures. The dose distribution characteristic or the robustness indicator may additionally or alternatively be provided to the TPS. For example, if the dose distribution characteristic or the robustness indicator satisfies a specific robustness criterion indicating the treatment plan under evaluation is robust, then the treatment plan may be stored in the memory 116 (as the radiation therapy treatment plan 142) and deployed in radiotherapy treatment of the patient. However, if the treatment plan does not satisfy the specific robustness criterion, then the user may reject the treatment plan, or modify the treatment plan such as adding a treatment margin or changing an irradiation direction. In an example, a recommendation for accepting, rejecting, or modifying the treatment plan may be automatically generated and displayed on the display device 134, prompting the user for input. Examples of the DVH graph and various dose distribution characteristics are discussed below, such as with reference to FIG. 9.

In some examples, the processor 114 may utilize software programs 144 to generate intermediate data such as updated parameters to be used, for example, by a machine learning model, such as a neural network model; or generate intermediate 2D or 3D images, which may then subsequently be stored in memory 116. The processor 114 may subsequently then transmit the executable radiation therapy treatment plan 142 via the communication interface 118 to the network 120 to the radiation therapy device 130, where the radiation therapy plan may be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software programs 144 when executed may train a boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processor 114 may be a special-purpose processor, rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™ The processor 114 may also include accelerated processing units such as the Xeon Phi™ family manufactured by Intel™ The disclosed examples are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory 116, to perform various operations, processes, methods that will be explained in greater detail below.

The memory 116 can store medical images 146. In some examples, the medical images 146 may include one or more MR images (e.g., 2D MRI, 3D MRI, 2D streaming MRI, four-dimensional (4D) MRI, 4D volumetric MRI, 4D cine MRI, etc.), functional MR images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), aperture images, graphical aperture image representations of MLC leaf positions at different gantry angles, and the like. Further, the medical images 146 may also include medical image data, for instance, training images, and ground truth images, contoured images, and dose images. In an example, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the data processing device 112 may use to perform operations consistent with the disclosed examples.

The memory 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices. Further, the memory 116 may store an entire software application, or only a part of a software application, that are executable by the processor 114. For example, the memory 116 may store one or more radiation therapy treatment plans 142.

The data processing device 112 can communicate with the network 120 via the communication interface 118, which can be communicatively coupled to the processor 114 and the memory 116. The communication interface 118 may provide communication connections between the data processing device 112 and radiotherapy system 100 components (e.g., permitting the exchange of data with external devices). For instance, the communication interface 118 may in some examples have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber. USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit data processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3(141). Systems S1, S2, and S3 may be identical to data processing device 112 or may be different systems. In some examples, one or more of systems in network 120 may form a distributed computing/simulation environment that collaboratively performs the examples described herein. In some examples, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 can allow data transmission between the data processing device 112 and a number of various other systems and devices, such as the OIS 128, the radiation therapy device 130, and the image acquisition device 132. Further, data generated by the OIS 128 and/or the image acquisition device 132 may be stored in the memory 116, the database 124, and/or the hospital database 126. The data may be transmitted/received via network 120, through communication interface 118 in order to be accessed by the processor 114, as required.

The data processing device 112 may communicate with the database 124 through network 120 to send/receive a plurality of various types of data stored on database 124. For example, the database 124 may store machine data associated with a radiation therapy device 130, image acquisition device 132, or other machines relevant to radiotherapy. The machine data information may include control points, such as radiation beam size, arc placement, beam on and off time duration, machine parameters, segments, MLC configuration, gantry speed. MRI pulse sequence, and the like. The database 124 may be a storage device and may be equipped with appropriate database administration software programs. One skilled in the art would appreciate that database 124 may include a plurality of devices located either in a central or a distributed manner.

In some examples, the database 124 may include a processor-readable storage medium (not shown). While the processor-readable storage medium in an example may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

The processor 114 may communicate with the database 124 to read images into the memory 116, or store images from the memory 116 to the database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) data, projection images, graphical aperture images, etc.) that the database 124 received from image acquisition device 132. Database 124 may store data to be used by the processor 114 when executing software program 144, or when creating radiation therapy treatment plans 142. The data processing device 112 may receive the imaging data, such as a medical image 146 (e.g., 2D MRI slice images. CT images, 2D Fluoroscopy images, X-ray images, 3DMR images, 4D MR images, projection images, graphical aperture images, etc.) either from the database 124, the radiation therapy device 130 (e.g., an MR-linac), and or the image acquisition device 132 to generate a treatment plan 142.

In an example, the radiotherapy system 100 may include an image acquisition device 132 that can acquire medical images (e.g., MR images, 3D MRI, 2D streaming MRL, 4D volumetric MR, CT images, cone-Beam CT. PET images, functional MR images (e.g., fMRI, DCE-MRI and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 132 can be also stored by the data processing device 112, as medical image 146 in memory 116.

In an example, for example, the image acquisition device 132 may be integrated with the radiation therapy device 130 as a single apparatus. For example, a MR imaging device can be combined with a linear accelerator to form a system referred to as an "MR-linac." Such an M R-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, may include one or more parameters (e.g., a 2D slice thickness, an orientation, and a location, etc.). In an example, the image acquisition device 132 can acquire a 2D slice in any orientation. For example, an orientation of the 2D slice may include a sagittal orientation, a coronal orientation, or an axial orientation. The processor 114 can adjust one or more parameters, such as the thickness and/or orientation of the 2D slice, to include the target organ and/or target tumor. In an example, 2D slices can be determined from information such as a 3D MRI volume. Such 21) slices can be acquired by the image acquisition device 132 in "real-time" while a patient is undergoing radiation therapy treatment, for example, when using the radiation therapy device 130, with "real-time" meaning acquiring the data in at least milliseconds or less.

The data processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume (DVH) information, number of radiation beams used during therapy, dose per beam, and the like.

The processor 114 may generate the radiation therapy treatment plan 142 by using software programs 144 such as treatment planning software (e.g., Monaco®, manufactured by Elekta AB of Sweden). In order to generate the radiation therapy treatment plans 142, the processor 114 may communicate with the image acquisition device 132 (e.g., a CT device, an MRI device, a PET device, an X-ray device, an ultrasound device, etc.) to access images of the patient and to delineate a target, such as a tumor. In some examples, the delineation of one or more OARs, such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MR images, CT images. PET images, fMR images, X-ray images, ultrasound images, radiotherapy portal images. SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as Monaco® manufactured by Elekta AB of Sweden) or automatically (e.g., using a program such as the Atlas-based auto-segmentation software, ABAS™, manufactured by Elekta AB of Sweden). In certain examples, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor. OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). The result of inverse planning may constitute a radiation therapy treatment plan 142 that may be stored in memory 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the data processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen or any type of device that a user may input information to radiotherapy system 100. Alternatively, the display device 134 and the user interface 136 may be integrated into a device such as a tablet computer.

Furthermore, any and all components of the radiotherapy system 100 may be implemented as a virtual machine (e.g., VMWare. Hyper-V, and the like). For instance, a virtual machine can be software that functions as hardware. Therefore, a virtual machine may include at least one or more virtual processors, one or more virtual memories, and one or more virtual communication interfaces that together function as hardware. For example, the data processing device 112, the OIS 128, the image acquisition device 132 could be implemented as a virtual machine. Given the processing power, memory, and computational capability available, the entire radiotherapy system 100 could be implemented as a virtual machine.

Figure 2A:
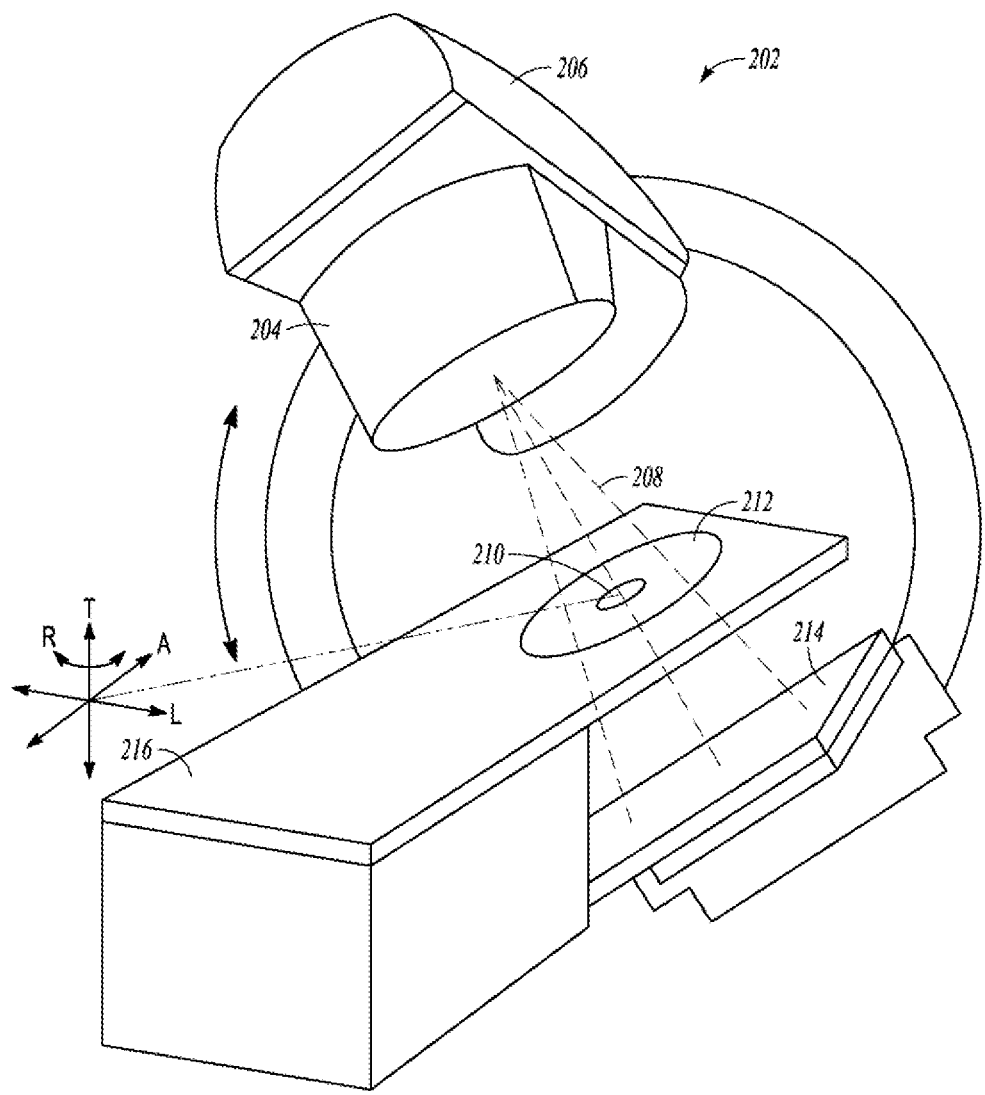
FIG. 2A illustrates an exemplary radiotherapy system that can provide a therapy beam.

FIG. 2A illustrates an exemplary radiation therapy device 202 that may include a radiation source (e.g., an X-ray source or a linac), a couch 216, an imaging detector 214, and a radiation therapy output 204. The radiation therapy device 202 may be configured to emit a radiation beam 208 to provide therapy to a patient. The radiation therapy output 204 may include one or more attenuators or collimators, such as an MLC. A patient can be positioned in a region 212 and supported by the couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around the couch 216 when the couch 216 is inserted into the treatment area. In an example, the gantry 206 may be continuously rotatable around the couch 216 when the couch 216 is inserted into the treatment area. In another example, the gantry 206 may rotate to a predetermined position when the couch 216 is inserted into the treatment area. For example, the gantry 206 can be configured to rotate the therapy output 204 around an axis ("A"). The couch 216 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can target the tumor. The MLC may be integrated with the gantry 206 to deliver the radiation beam 208 of a certain shape.

The coordinate system (including axes A. 7T and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

The linac system may have an imaging detector 214 that is preferably opposite the radiation therapy output 204. In an example, the imaging detector 214 can be located within a field of the therapy beam 208. The imaging detector 214 can maintain alignment with the therapy beam 208. The imaging detector 214 can rotate about the rotational axis as the gantry 206 rotates. In an example, the imaging detector 214 can be a flat panel detector (e.g., a direct detector or a scintillator detector). In this manner, the imaging detector 214 can monitor the therapy beam 208, or generate an image of the patient's anatomy. The control circuitry of radiotherapy device 202 may be integrated within system 100 or remote from it.

In an illustrative example, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, the couch 216, or the therapy output 204. The therapy deliveries can occur sequentially, but can intersect in a desired therapy locus on or within the patient, such as at the isocenter 210. A prescribed dose of radiation therapy can thereby be delivered to the therapy locus while damage to tissue near the therapy locus can be reduced or avoided.

Figure 2B:
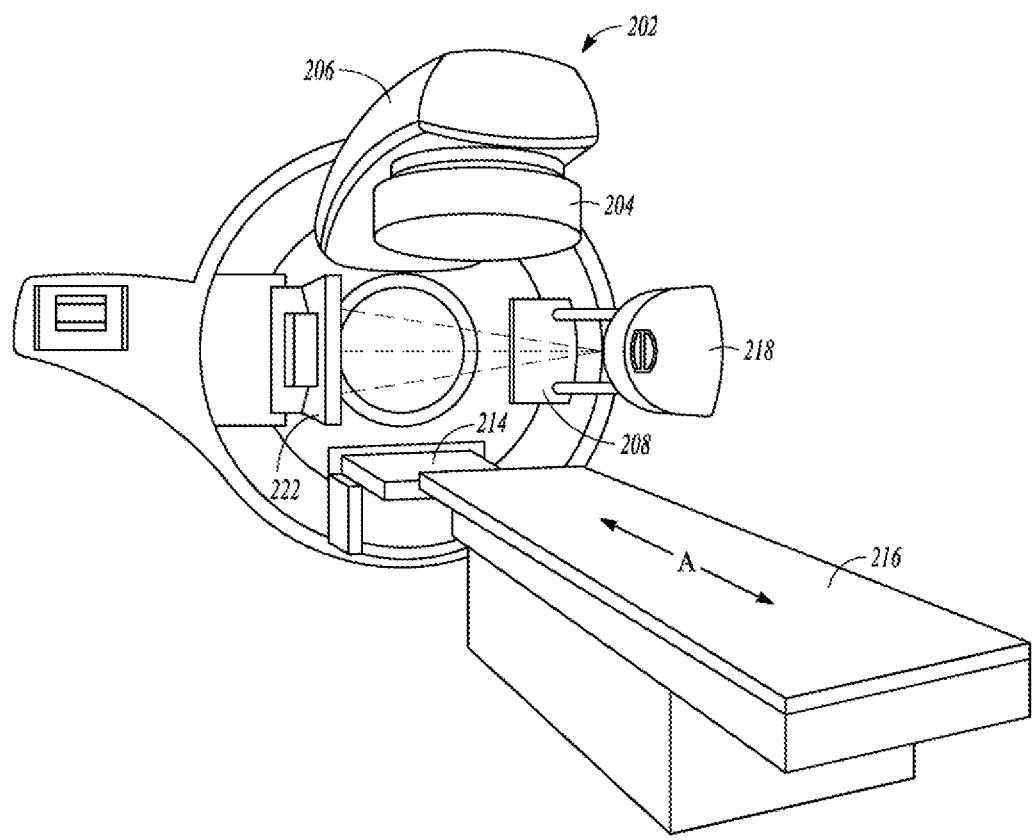
FIG. 2B illustrates an exemplary combined system including a computed tomography (CT) imaging system and a radiation therapy system.

FIG. 2B illustrates the exemplary radiation therapy device 202 that combines a radiation system (e.g., a linac) and a CT imaging system. The radiation therapy output 204 may include an MLC (not shown). The CT imaging system may include an imaging X-ray source 218, such as providing X-ray energy in a kiloelectron-Volt (keV) energy range. The imaging X-ray source 218 can provide a fan-shaped and/or a conical beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam, for imaging.

As illustrated in FIG. 2B, the radiation therapy output 204 and the X-ray source 218 can be mounted on the same rotating rotation mechanism, rotationally-separated from each other by 90 degrees. In some examples, two or more X-ray sources can be mounted along the circumference of the rotation mechanism, such that each has its own detector arrangement to provide multiple angles of diagnostic imaging concurrently. Similarly, multiple radiation therapy outputs 204 may be provided.

Figure 3:
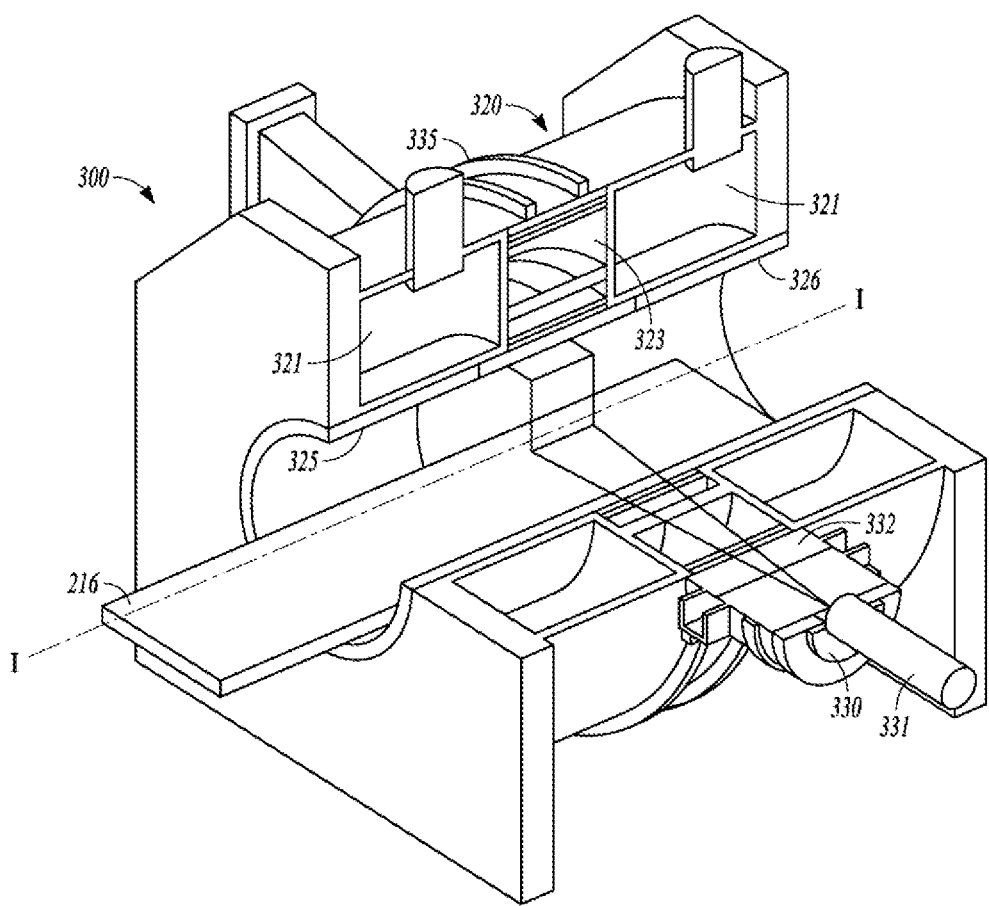
FIG. 3 illustrates a partially cut-away view of an exemplary combined system including a nuclear magnetic resonance (MR) imaging system and a radiation therapy system.

FIG. 3 illustrates an exemplary radiotherapy system 300 that combines a radiation system (e.g., a linac) and a nuclear MR imaging system, also referred to as an MR-linac system. The system 300 may include a couch 216, an image acquisition device 320, and a radiation delivery device 330. The system 300 can deliver radiation therapy to a patient in accordance with a radiotherapy treatment plan, such as the treatment plan 142 generated and stored in the memory 116. In some examples, the image acquisition device 320 may correspond to the image acquisition device 132 in FIG. 1 that may acquire images of a first modality (e.g., an MR image) or destination images of a second modality (e.g., a CT image).

The couch 216 may support a patient during a treatment session. In some implementations, the couch 216 may move along a horizontal translation axis (labelled "I"), such that the couch 216 can move the patient resting on the couch 216 into and/or out of the system 300. The couch 216 may also rotate around a central vertical axis of rotation, transverse to the translation axis. To allow such movement or rotation, the couch 216 may have motors (not shown) enabling movement of the couch 216. A controller (not shown) may control these movements or rotations in order to properly position the patient according to a treatment plan.

In some examples, the image acquisition device 320 may include an MR imaging machine that can acquire 2D or 3D MR images of the patient before, during, and/or after a treatment session. The image acquisition device 320 may include a magnet 321 for generating a primary magnetic field for magnetic resonance imaging. The magnetic field lines generated by operation of the magnet 321 may run substantially parallel to the central translation axis "I". The magnet 321 may include one or more coils with an axis that runs parallel to the translation axis "I". In some examples, the one or more coils in magnet 321 may be spaced such that a central window 323 of magnet 321 is free of coils. In other examples, the coils in magnet 321 may be thin enough or of a reduced density such that they are substantially transparent to radiation of the wavelength generated by radiotherapy device 330. In some examples, the image acquisition device 320 may also include one or more shielding coils, which may generate a magnetic field outside the magnet 321 of approximately equal magnitude and opposite polarity in order to cancel or reduce any magnetic field outside of the magnet 321. As described below, a radiation source 331 of radiotherapy device 330 may be positioned in the region where the magnetic field is cancelled, at least to a first order, or reduced.

The image acquisition device 320 may also include two gradient coils 325 and 326, which may generate a gradient magnetic field that is superposed on the primary magnetic field. The coils 325 and 326 may generate a gradient in the resultant magnetic field that allows spatial encoding of the protons so that their position can be determined. The gradient coils 325 and 326 may be positioned around a common central axis with the magnet 321 and may be displaced along that central axis. The displacement may create a gap, or window, between the coils 325 and 326. In examples where the magnet 321 includes a central window 323 between the coils, the two windows may be aligned with each other.

In some examples, the image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain examples and is not intended to be limiting.

The radiotherapy device 330 may include the radiation source 331 (e.g., an X-ray source or a linac), and a collimator such as an MLC 332. A collimator is a beam-limiting device that can help to shape the beam of radiation emerging from the machine and can limit the maximum field size of a beam. The MLC 332 can be used for shaping, directing, or modulating an intensity of a radiation therapy beam to the specified target locus within the patient. The MLC 332 may include metal collimator plates, also known as MLC leaves, which slide into place to form the desired field shape. The radiotherapy device 330 may be mounted on a chassis 335. One or more chassis motors (not shown) may rotate chassis 335 around the couch 216 when the couch 216 is inserted into the treatment area. In an example, chassis 335 may be continuously rotatable around the couch 216, when the couch 216 is inserted into the treatment area. The chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of the couch 216, image acquisition device 320, and radiotherapy device 330. The control circuitry of radiotherapy device 330 may be integrated within system 3M) or remote from it.

During a radiotherapy treatment session, a patient may be positioned on the couch 216. System 300 may then move the couch 216 into the treatment area defined by magnetic 321 and coils 325, 326, and chassis 335. Control circuitry may then control the radiation source 331. MLC 332, and the chassis motor(s) to deliver radiation to the patient through the window between coils 325 and 326 according to a radiotherapy treatment plan.

The radiation therapy output configurations illustrated in FIGS. 2A-2B and 3, such as the configurations where a radiation therapy output can be rotated around a central axis (e.g., an axis "A"), are for the purpose of illustration and not limitation. Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

Figure 4:
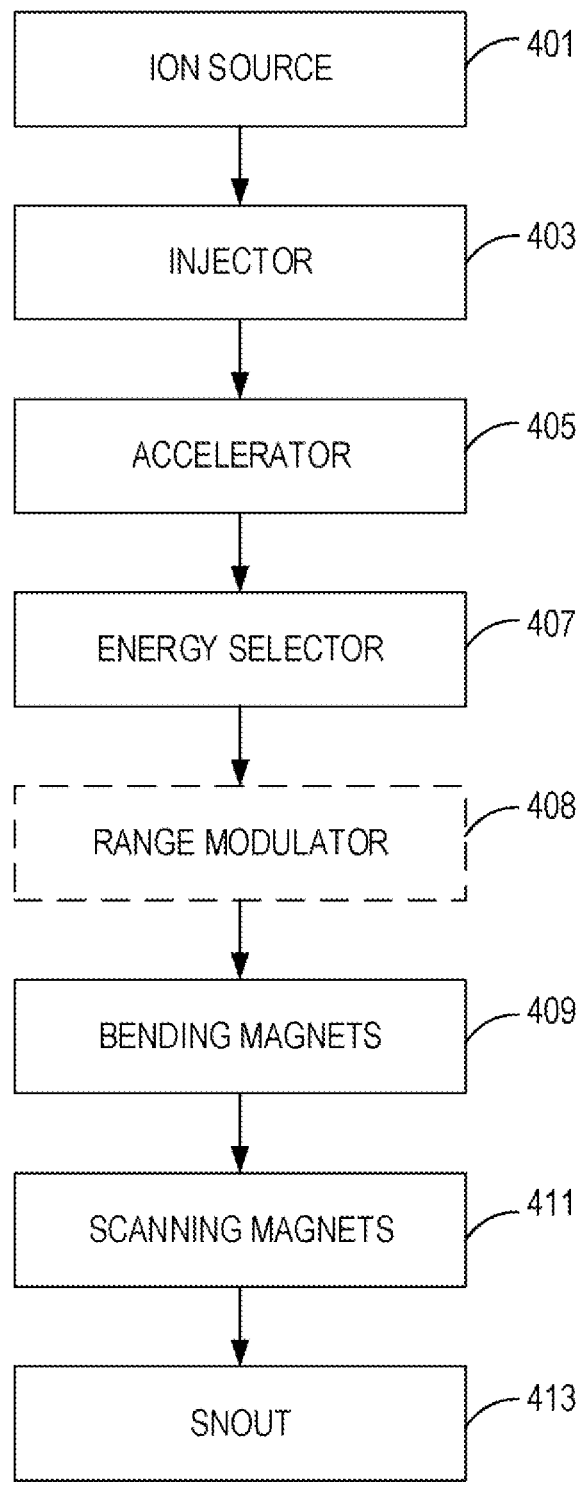
FIG. 4 illustrates an example of a particle treatment system configured to provide proton therapy.

FIG. 4 illustrates an example of a particle treatment system 400 configured to provide a proton therapy beam. The particle treatment system 400 includes an ion source 401, an injector 403, an accelerator 405, an energy selector 407, a plurality of bending magnets 409, a plurality of scanning magnets 411, and a snout 413.

The ion source 401, such as a synchrotron (not shown) may be configured to provide a stream of particles, such as protons. The stream of particles is transported to an injector 403 that provides the charged particles with an initial acceleration using a Coulomb force. The particles are further accelerated by the accelerator 405 to about 70% of the speed of light. The acceleration provides energy to the particles, which determines the depth within tissue the particles may travel. The energy selector 407 (e.g., a range scatter) may be used to select the energies of the protons to be delivered to the patient. In an embodiment called passive scattering, an optional range modulator 408 (e.g., also called a ridge filter or a range modulation wheel) may be utilized to broaden the beam to fit the tumor. After selecting energies, a set of bending magnets 409 may be utilized to transport the stream of protons into a radiation therapy treatment room of a hospital. Further, scanning magnets 411 (e.g., x-y magnets) are used to spread the proton beam to, or trace, an exact image of the tumor shape. A snout 413 or components of the snout 413 (e.g., a collimation device) may be used to further shape the proton beam. In various embodiments, the stream of particles may be composed of carbon ions, pions, or positively charged ions.

Figure 5:
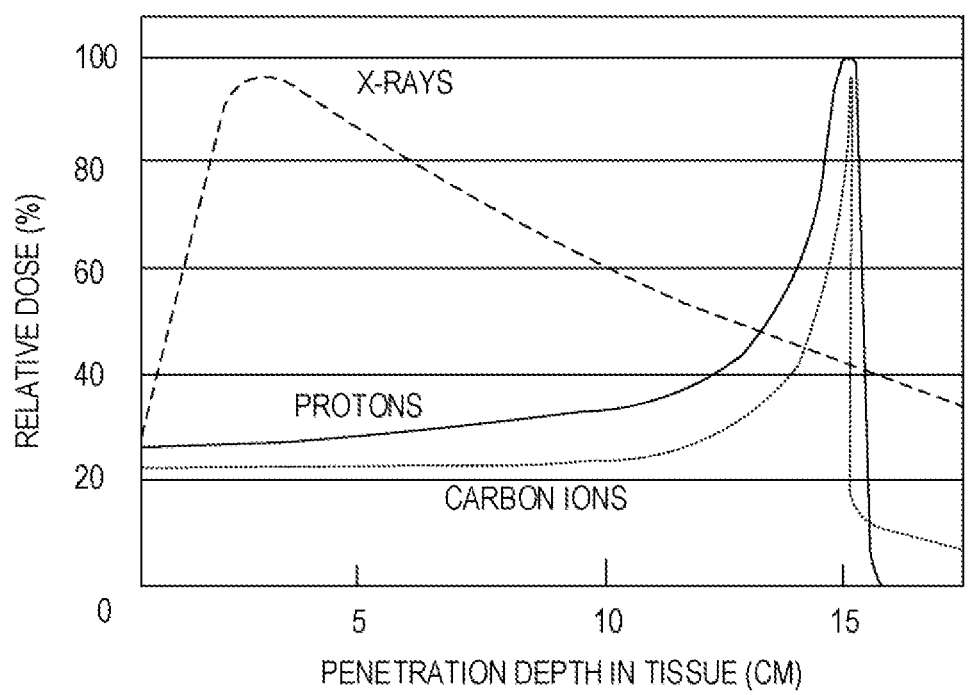
FIG. 5 is a diagram illustrating radiation dose depths (depth-dose distributions) for various types of particles in human tissue.

FIG. 5 is a diagram illustrating radiation dose depths (depth-dose distributions) for various types of particles in human tissue. By way of example, the relative depth of penetration into human tissue of photons (e.g., X-rays) versus protons versus carbon ions is shown (e.g., including any radiation dose provided at a distance beneath the surface, including secondary radiation or scatter). Each radiation dose is shown relative to the peak dose for a proton beam having a single energy which has been set to 100%.

The dose delivered by the mono-energetic (e.g., single energy) proton beam can be conformed to the target in depth. Because protons are massive and charged particles, they directly ionize atomic electrons. In each interaction, the proton loses only a small amount of its energy. Most of the protons travel in an almost straight line and traverse the body until all of their energy is lost. The depth at which the proton comes to rest depends on its initial energy. Most of the proton energy is deposited just before the end of its range, which results in a peak in the depth-dose distribution that is known as the Bragg peak. As shown in FIG. 5, the proton beam indicates a plateau region starting at approximately 25% that gradually increases until approximately 10 cm depth in tissue where it rapidly increases to the Bragg Peak at 15 cm and then advantageously falls to zero within a short distance. No additional dose is delivered at the end of the Bragg peak.

The photon beam (e.g., labelled as X-rays) indicates the initial build up due to electron scatter (e.g., the primary means by which X-rays deliver dose to tissue is through transfer of energy to electrons in the tissue). This is followed by an exponential fall off, which continues past the distal edge of the target, which is at approximately 15 cm depth in the diagram. The X-ray beam has an entrance (skin) dose set to match that of the proton beam. With normalization (e.g., scaling) at 15 cm depth, the dose due to X-rays is at 40% of the dose provided by proton beam, while the X-ray beam has a peak dose of greater than 95% ("near" 100%) at approximately 3 cm depth. If the X-ray data is renormalized to achieve 100% dose at 15 cm, the peak dose at approximately 3 cm depth would be approximately 240%, in a location where dose is not desired (e.g., prior to the target). Therefore, with X-rays, a considerable amount of dose is delivered prior to the target and an appreciable amount of dose is delivered past the target. The proton beam can deliver the same dose to target while delivering less than half of the integral dose of the x-ray beam.

The mono-energetic carbon beam shows a plateau region at the entrance dose that is lower than the proton beam. The carbon beam has a sharper Bragg Peak that falls more precipitously than the proton beam, but the carbon beam has a tail (e.g., known as a "spallation tail", where some of the Carbon nuclei shatter in to Helium ions) that has approximately 10% additional dose, or less, past the desired target by several centimeters. The carbon ion beam has an undesired entrance and skin dose compared to the proton beam, but the carbon ion beam has a non-trivial dose delivered past the target.

Figure 6:
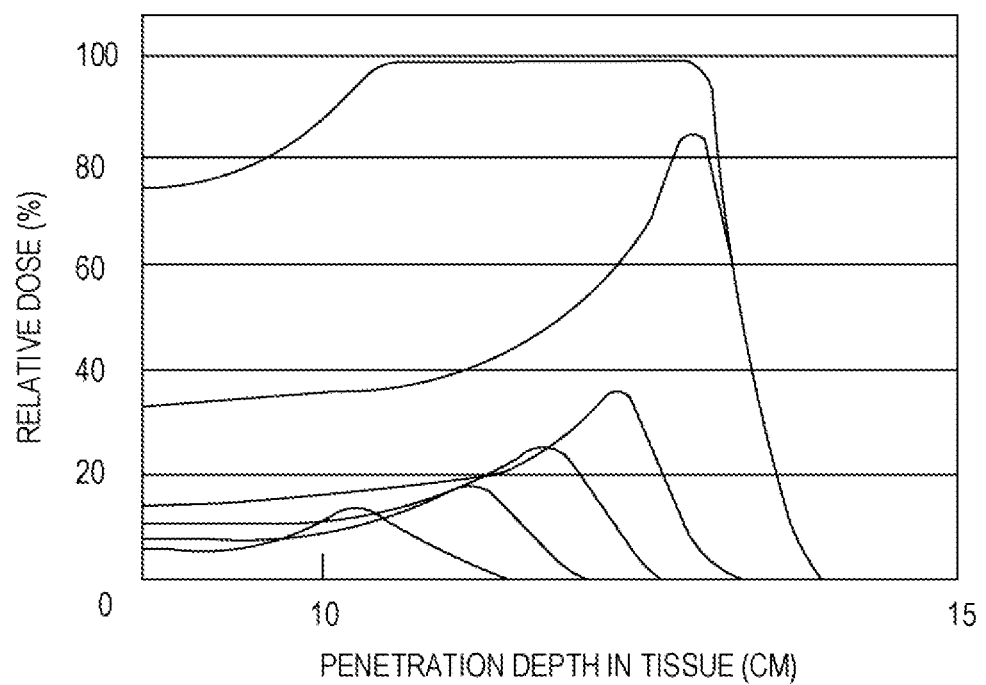
FIG. 6 is a diagram illustrating a spread-out Bragg peak (SOBP).

FIG. 6 is a diagram illustrating a spread-out Bragg peak (SOBP) representing a relative depth dose curve for the combination of a set of proton beams of various initial energies each of which has had some spread in energy (e.g., variable absorption of energy in tissue). The desired result of having a uniform dose for a target of a particular thickness. As shown, the target is shown with a proximal depth of approximately 10 cm, a distal depth of approximately 13 cm, and a target thickness of approximately 3 cm. Within the target, the dose is quite uniform (with an average normalized at 100%). The diagram does not start at 0 cm depth and is not explicitly showing the entrance (skin) dose, but the nature of the entrance region of proton beams is a relatively flat depth dose curve. Typically, the entrance (skin) dose will be approximately 70% of the target dose (e.g., shown at the far right edge of the x-axis). A SOBP may be obtained using a variety of approaches, including using a scattered proton beam with modulation of the energy (variable absorption) utilizing a variety of devices (e.g., a static ridge filter or a dynamic range modulation wheel), or by selection of a number of mono-energetic proton beams that do not undergo scatter.

Figure 7:
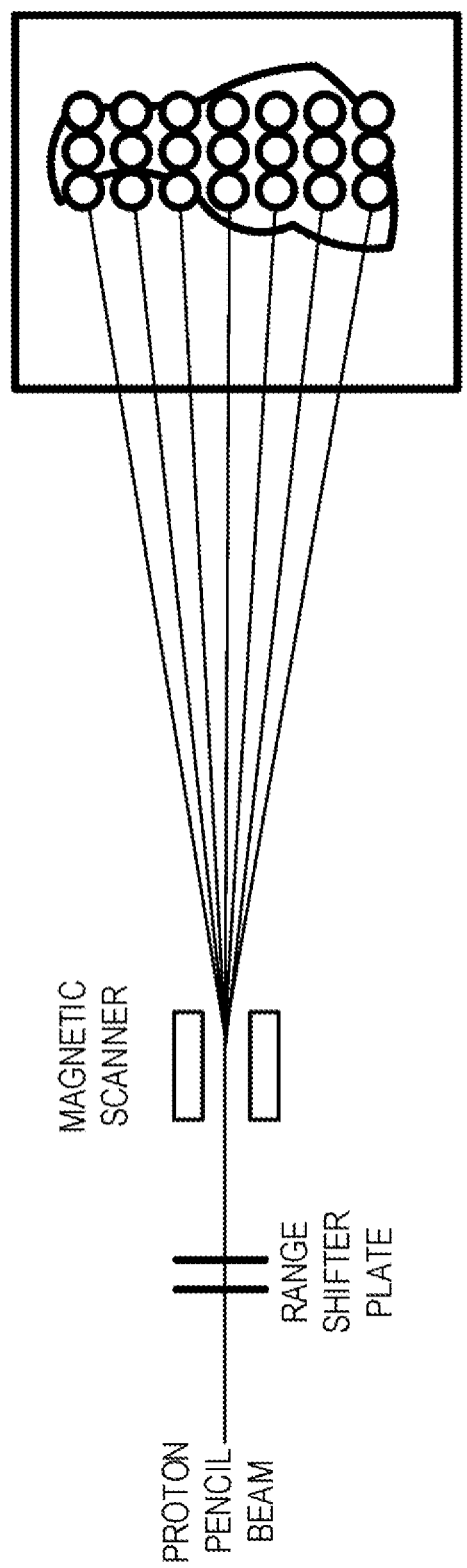
FIG. 7 illustrates an example of an active scanning proton beam delivery system.

FIG. 7 illustrates a diagrammatic representation of an active scanning proton beam delivery system. As shown, a single layer of a pencil beam scan is being delivered, with a grid of spots depicted on a patient in conjunction with a contour of the cross-sectional area to which particles are to be delivered. An incoming mono-energetic proton beamlet has a specified amount of its energy absorbed by the Range Shifter (e.g., in FIG. 7 it is a Range Shifter plate), resulting in a beamlet with the desired energy to achieve a certain depth for the Bragg Peak in the patient to treat the specified layer. A magnetic scanner, which has the ability to deflect the particles in both a vertical and a horizontal direction. The strength of the magnetic fields may be adjusted to control the deflection in the direction perpendicular to the magnetic field and the incoming beamlet. The rate at which the magnetic field strengths may be adjusted determines the rate at which the scanning may take place. For instance, the intensity of the proton beamlet in combination with the scanning rate determines how much dose may be delivered to a specific area (e.g., in FIG. 7, a "spot") in a particular amount of time (e.g., particles/unit area). In theory, the magnetic field strengths may be adjusted independently of each other (in a fashion similar to the children's toy "Etch a Sketch®", provided by Spin Master™, Toronto, Canada; with the pencil beamlet intensity being a variable not available in the children's toy). The most common scheme for scanning is to scan in one direction quickly and to scan in the perpendicular direction more slowly in a raster fashion, similar to how early televisions were controlled (e.g., Cathode Ray Tube (CRT), which use electrons instead of protons), but arbitrary patterns may be scanned (similar to the previously mentioned toy). Delivery of distinct spots is achieved by incrementing the scanning magnetic field strength and throttling the pencil beam intensity between increments.

As described above, a treatment plan needs to be robust to range uncertainties including systematic and random patient setup errors so as to ensure the target volume receives a tumoricidal dose, and that the OAR doses are kept below complication thresholds. Robustness evaluation of a treatment plan against setup and range uncertainties can be helpful in a treatment planning process, and may influence clinical decision making.

The robustness of a radiotherapy treatment plan may be evaluated in a radiation simulation process comprising multiple simulated scenarios. The simulated scenarios may include dose simulations under a nominal condition and one or more artificially imposed uncertainty conditions that deviate from the nominal condition. Simulated scenarios corresponding to the uncertainty conditions are also referred to as deviation scenarios. Dose distribution may be generated for each simulated scenario using the treatment plan under evaluation. One example of the dose distribution is a dose-volume histogram (DVH) that relates radiation dose to volume of an anatomical structure. For a specific anatomical structure, a cluster of DVHs may be calculated under different simulated scenarios (e.g., a nominal condition and one or more uncertainty conditions). For example, a DVH cluster may be calculated for a target structure to receive radiation treatment, and one or more separate DVH clusters may be calculated respectively for one or more structures at risk (e.g., one or more OARs) to avoid radiation treatment.

The artificially imposed uncertainty conditions may include range uncertainties, patient setup errors, or a combination thereof. In an example, the nominal condition includes a nominal location of the anatomical structure, and the deviation scenarios may be simulated for a treatment under a systematic setup error represented by one or more positional deviations from the nominal location of the anatomical structure. The positional deviation may include deviation in one or more of +/−X, +/−Y, or +/−Z directions. In another example, the nominal condition includes a nominal CT Hounsfield unit to proton stopping power (HU-SP) conversion. The deviation scenarios may be simulated for a treatment under Hounsfield Unit (HU) range uncertainties represented by one or more percentile deviations from the nominal HU-SP conversion. In yet another example, the deviation scenarios may be simulated for a treatment under a combination of a systematic setup error and a HU uncertainty. For example, with six distinct systematic setup errors (e.g., 3 mm setup error in each one of +X, −X, +Y, −Y, +Z, and −Z directions) and two distinct HU range uncertainty values (e.g., 3% and −3%), twelve deviation scenarios may be simulated, and dose distributions such as DVHs may be calculated respectively for those deviation scenarios.

Figure 8:
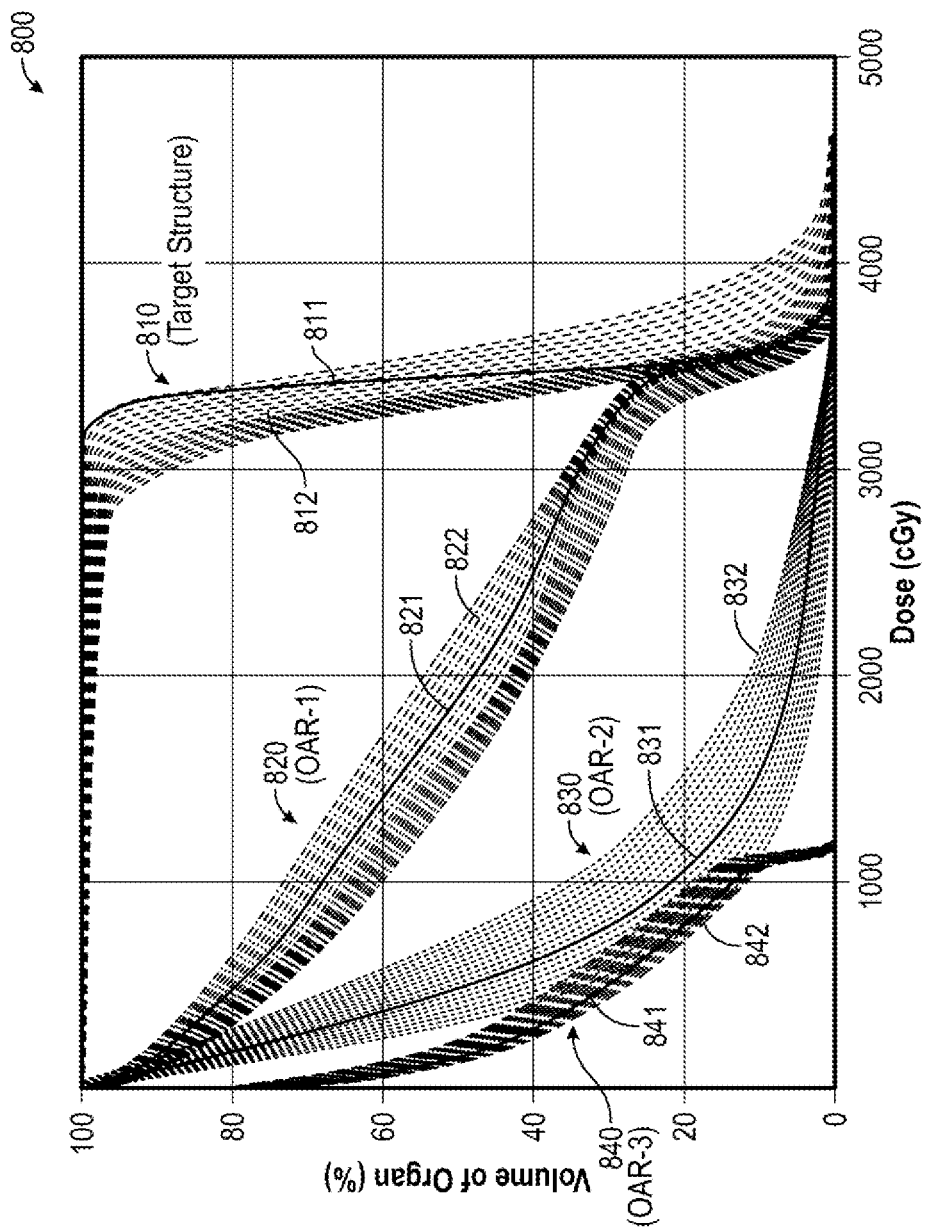
FIG. 8 is a diagram illustrating a conventional two-dimensional DVH graph.

The DVHs may be used to evaluate robustness of the radiotherapy treatment plan used for generating the DVHs. FIG. 8 illustrates a conventional two-dimensional (2D) DVH graph 800 including clusters of DVHs generated for different structures under various simulated scenarios, using data (e.g., CT scan) generated by the therapy planning system in accordance with the treatment plan to be evaluated. The 2D DVH graph 800 may be displayed on a user interface, such as the display device 134 of the system 100. In this example, a DVH cluster 810 for the target structure (also referred to as "target DVHs"), and three other DVH clusters 820, 830, and 840 for three distinct structures at risk OAR-1, OAR-2, and OAR-3, respectively, are shown in the 2D DVH graph 800. Each cluster includes a respective nominal DVH (e.g., 811, 821, 831, and 841) corresponding to the nominal condition free of artificially introduced error or uncertainty, and a number of uncertainty DVHs (also referred to as deviation DVHs, e.g., 812, 822, 832, and 842) corresponding to artificially imposed uncertainty conditions, such as range uncertainties, patient setup errors, or a combination thereof. By way of example, the uncertainty DVHs may be created under certain deviations from a nominal position in one or more of +/−X, +/−Y, or +/−Z directions, a HU uncertainty values, or a combination of deviations from the nominal position and the HU uncertainty values, as discussed above.

Each DVH represents volume of structure receiving a dose greater than or equal to a particular dose or dose range. The x-axis of the DVH graph represents dose bins each representing a dose range in the unit of gray (Gy) or centigray (cGy). The y-axis of a DVH graph represents volume of structure, or relative volume represented by percentage of total volumes of the structure being considered, that receives the dose greater than or equal to the corresponding dose bin. The volume of structure can be determined by the total number of voxels (e.g., from a CT scan) characterized by a specified range of dosage for the organ considered. With small bin sizes, the cumulative DVH takes on the appearance of a smooth line graph, as shown in FIG. 8. The lines always slope and start from top-left to bottom-right. For a structure receiving a very homogenous dose (100% of the volume receiving exactly 10 Gy, for example) the DVH will appear as a horizontal line at the top of the graph, at 100% volume as plotted vertically, with a vertical drop at 10 Gy on the horizontal axis. Ideally, the dose received by the target structure would cover 100% of the volume of target (i.e., dose completely irrigating the target), and the dose received by an OAR would have 0% of the volume of OAR (i.e., dose not irritating the OAR).

A clinical user may find it challenging to review and interpret the dose distributions using the 2D DVH graph 800, which includes DVH clusters corresponding to multiple structures, each including DVHs under multiple simulated scenarios (e.g., a nominal condition and multiple uncertainty conditions). For example, DVHs for different structures may overlap to each other, making it difficult to distinguish between DVHs for different structures and determine their differences. For a particular structure, the overlay of a cluster of DVHs under different scenarios (e.g., nominal and uncertainty conditions) does not provide easily digestible information about treatment plan robustness, and there are few qualitative or quantitative indicators of robustness. The clinical user also lacks flexibility to manipulate the DVH graph or a DVH cluster for better data visualization and interpretation.

Figure 9:
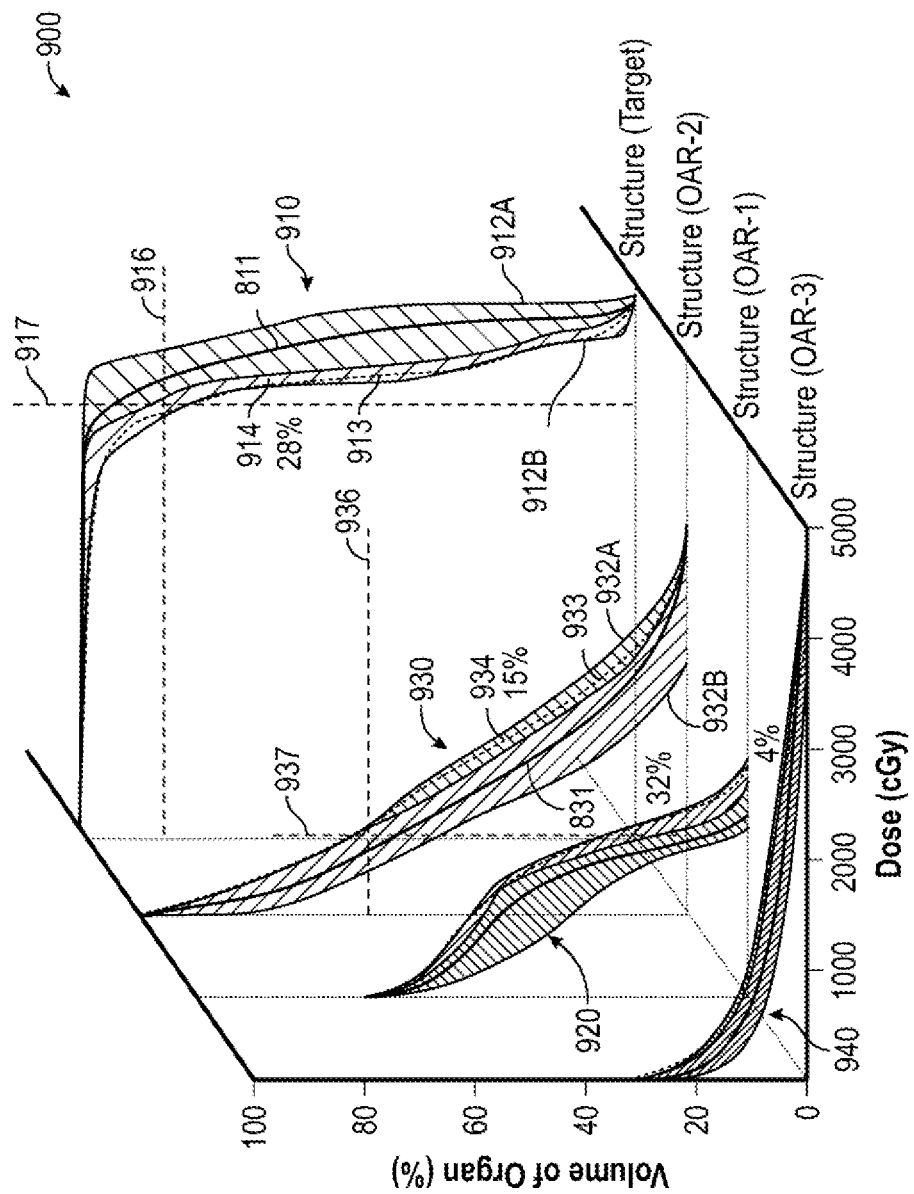
FIG. 9 is a diagram illustrating an example of a three-dimensional DVH graph spanned in a dose-volume-structure space.

FIG. 9 illustrates an example of a three-dimensional (3)) DVI graph 900, which is an improvement over the conventional 2D DVH graph 800. Compare to the 2D DVH graph 800, the 3D DVIH graph 900 includes a "structure" dimension representing different anatomical structures involved in the dose simulation, such as a target structure and one or more OARs. Instead of overlaying DVH information of different structures (e.g., DVH clusters 810, 820, 830, and 840) on the same 2D volume-dose plane, in FIG. 9 the DVH information of different structures may be stacked along the "structure" axis on a 3D dose-volume-structure space. Spreading the DVH information along the "structure" axis can improve the visualization and recognition of differences in dose distribution between different structures and across different simulated scenarios, thereby improving the evaluation of treatment plan robustness.

Another improvement over the conventional 2D DVH graph 800, as illustrated in the 3D DVH graph 900, includes dose distribution characteristics generated and presented on the DVH graph. For example, in lieu of or in addition to the DVH clusters (e.g., 810, 820, 830, and 840) of raw DVH curves, the 3D DVH graph shows additional DVH characteristics of target structure 910, and DVH characteristics of OAR-1 920, OAR-2 930, and OAR-3 940. As illustrated in FIG. 9, the DVH characteristics of target structure 910 may include the nominal DVH 811 (solid line) and one or more statistical features generated from the DVH cluster 810. Similarly, the DVH characteristics 920, 930, and 940 may each include respective nominal DVHs 821, 831, or 841 (solid lines) and one or more statistical features generated respectively from the DVH clusters 820, 830, or 840. Based on the DVH characteristics, the processor 114 may generate a robustness indicator of the treatment plan under evaluation.

Examples of the DVH characteristics and the robustness indicator generated therefrom are discussed as follows. In some examples, a composite robustness indicator may be generated using a combination of two or more different DVH characteristics as discussed herein.

DVH Band

A DVH band represents a DVH range due to uncertainty conditions involved in the dose simulation. Using the target structure as an example, the DVH characteristics of target structure 910 includes a DVH band 912 bounded by a first boundary DVH 912A and a second boundary DVH 912B. The first boundary DVH 912A represents the highest received dose across a range of volumes of the target structure. The second boundary DVH 912B represents the lowest received dose across a range of volumes of the target structure. The first and second boundary DVHs may be identified from the DVH cluster 810. For example, the first boundary DVH 912A may be identified as the right-most DVH with respect to the nominal DVH 811, indicating a higher dose across all volumes (X-axis from 0-100%) of the target than the nominal DVH. The second boundary DVH 912B may be identified as the left-most DVH with respect to the nominal DVH 811, indicating a lower dose across all volumes of the target than the nominal DVH.

Alternatively, instead of being selected from the DVH cluster 810, the first or second boundary DVH may be calculated using the DVH cluster 810. In an example, the first boundary DVH 912A may be determined by taking the maximum dose across all the DVHs of the cluster 810 at each volume level from 0 to 100%. Similarly, the second boundary DVH 912B may be determined by taking the minimum dose across all the DVHs of the cluster 810 at each volume level from 0 to 100%. The boundary DVHs 912A and 912B thus determined are boundaries that enclose all the DVHs in the cluster 810.

A DVH range can be graphically represented by the DVH band bounded by the first boundary DVH 912A and the second boundary DVH 912B. Boundary DVHs and the DVH band enclosed thereby may be similarly determined, such as boundary DVHs 932A and 932B for OAR-2, as shown in FIG. 9.

A robustness indicator of the treatment plan under evaluation may be generated using the DVH band, the first boundary DVH 912A, or the second boundary DVH 912B. In an example, the robustness indicator can be computed using a "width" of the DVH band, such as a deviation $\Delta_B$ of the second boundary DVH from the first boundary DVH. In another example, the robustness indicator can be computed using a deviation $\Delta_{B1}$ of the first boundary DVH from the nominal DVH, or a deviation $\Delta_{B2}$ of the second boundary DVH from the nominal DVH. The deviation (e.g., $\Delta_B$, $\Delta_{B1}$, or $\Delta_{B2}$) can be measured at a specific volume (e.g., 90%), or be taken as the maximum deviation across the entire volume range of 0-100%. A narrower DVH band $\Delta_B$ or a narrow deviation $\Delta_{B1}$ or $\Delta_{B2}$ may indicate a higher robustness of the treatment plan. In some examples, the robustness indicator may be determined as combination (e.g., a weighted sum) of the DVH band width $\Delta B$ (or $\Delta_{B1}$ or $\Delta_{B2}$) of the target structure and the DVH band width $\Delta_B$ (or $\Delta_{B1}$ or $\Delta_{B2}$) of one or more OARs. The processor 114 may determine the treatment plan is robust if the robustness indicator satisfies a condition, such as falling below a threshold.

Extreme-Scenario DVH

For a specific anatomical structure, an extreme-scenario DVH may be generated using the cluster of DVHs created for that anatomical structure under different simulated scenarios. Using the target structure 910 as an example, the extreme-scenario DVH 913 (a dashed line) represents a DVH, identified from the DVH cluster 810, that most significantly deviate from a dosimetric criterion. The extreme-scenario DVH 913 is also referred to as a worst-scenario DVH. The dosimetric criterion may be defined using a reference volume 916 (e.g., 95%), a reference radiation dose 917 (e.g., 4200 cGy), or a combination of the reference volume 916 and the reference radiation dose 917.

In an example, the extreme-scenario DVH 913 may be determined as a DVH, identified from the DVH cluster 810, that corresponds to a minimum radiation dose received by the reference volume 916 (e.g., 95%) of the target structure. In another example, the extreme-scenario DVH 913 may be determined as the DVH that corresponds to a minimum tissue volume of the target structure that receives the reference radiation dose 917 (e.g., 4200 cGy). For instance, a clinical user may define the dosimetric criterion as 95% volume of the target structure receiving a dose level equal to or greater than 4200 cGy. The clinical user can then perform dose simulations including 20 deviation scenarios with distinct uncertainty conditions. Accordingly, the processor 141 can generate 21 DVHs, including one nominal DVI-H corresponding to the nominal condition, and 20 uncertainty DVHs corresponding to the 20 deviation scenarios. For a reference volume 916 of 95%, assuming the dose received by 95% of the volume of the target structure under different deviation scenarios is as follows: 4100 cGy (deviation scenario is 3 mm setup error in +X direction and 3% HU range uncertainty); 4120 cGy (deviation scenario is 3 mm setup error in −X direction and −3% HU range uncertainty); 4300 cGy (deviation scenario is 3 mm setup error in +Y direction and −3% HU range uncertainty); 4328 cGy (deviation scenario is 3 mm setup error in −Y direction and 3% HU range uncertainty); and 4428 cGy (deviation scenario is 3 mm setup error in +Z direction and 3% HU range uncertainty), etc. Then, the extreme-scenario DVH 913 may be identified as the DVH, among the cluster 810, that has the lowest dose received by 95% of the volume, which in this case is the DVH corresponding to 4100 cGy at 95% volume mark. The lowest dose received by 95% of volume always exists with 21 scenarios regardless of whether the result passes the dosimetric criterion or not. In an example, a clinical user may review the extreme-scenario to evaluate the robustness of the treatment plan in terms of dose received at the target structure without reviewing each and every simulated scenario (e.g., the DVHs of cluster 810).

For a structure at risk such as OAR-2 corresponding to the DVH cluster 830, an extreme-scenario DVH 933 (dashed line) may be determined as a DVH, among the DVH cluster 830, that corresponds to a maximum radiation dose received by a reference tissue volume 936 (e.g., 70%) of OAR-2. In another example, the extreme-scenario DVH may be determined as a DVH corresponding to a maximum tissue volume of the OAR-2 receiving a reference dose level 937 (e.g., 1000 cGy).

A robustness indicator of the treatment plan under evaluation may be generated using the extreme-scenario DVH. In an example, the robustness indicator may be determined using a deviation $\Delta_{WS}$ of the extreme-scenario DVH from the dosimetric criterion, such as the reference volume 916 or from the reference radiation dose 917. A smaller $\Delta_{WS}$ indicates a higher robustness of the treatment plan. In some examples, the robustness indicator may be computed using a combination (e.g., a weighted sum) of $\Delta_{WS}$ of the target structure and one or more $\Delta_{WS}$ of respective one or more OARs. The processor 114 may determine the treatment plan is robust if the robustness indicator satisfies a condition, such as falling below a threshold.

Out-of-Range DVHs

The DVH characteristics for each of the structures may include identification of one or more DVHs, among the respective DVH cluster, that fail to meet a dosimetric criterion, such as falling outside a tolerance margin with respect to the nominal DVH. The identified DVHs are referred to as "out-of-range DVHs." Compared to the extreme-scenario DVH which is one that most significantly deviates from a dosimetric criterion, the "out-of-range DVHs" include all those DVHs, among the DVH cluster of a particular structure, that fall outside a specific range according to a dosimetric criterion. Similar to the discussion above with respect to the extreme-scenario DVH, the dosimetric criterion may be defined using a reference volume 916 (e.g., 95%), a reference radiation dose 917 (e.g., 4200 cGy), or a combination of the reference volume 916 and the reference radiation dose 917.

The out-of-range DVHs for the target structure include those DVHs, among the DVH cluster 810, that have a radiation dose at a reference tissue volume falling below a reference radiation dose by a tolerance margin. For instance, for a reference volume of 95% and a reference radiation dose of 4200 cGy, assuming the dose received by 95% of the volume of the target structure under the nominal condition (corresponding to the nominal DVH 811) is 4350 cGy, and the dose received by 95% of the volume under different deviation conditions (corresponding to the deviation scenario DVHs 812) are 4100 cGy, 4120 cGy, 4150, 4200, 4300 cGy, 4320 cGy, 4380 cGy, 4400 cGy, etc. Then, for a tolerance margin of 20 cGy, only those deviation scenarios having a dose level, at 95% volume mark, less than 4180 cGy (the dose level of the nominal DVH which is 4200 cGy, less the margin of 20 cGy) are counted as the "out-of-range DVHs."

For a structure at risk such as OAR-2, the out-of-range DVHs may be similarly determined as those DVHs, among the DVH cluster 830, that have a radiation dose at a reference tissue volume (e.g., 95%) exceeding a reference radiation dose by a tolerance margin.

The out-of-range DVHs identified for a structure (the target structure or an OAR) may be repressed graphically by a sub-band covering the identified out-of-range DVHs, such as the out-of-range sub-band 914 within the DVH band bounded by 912A and 912B for the target structure, or the out-of-range sub-band 934 within the DVH band bounded by 932A and 932B for the OAR-2, as illustrated in FIG. 9.

In some examples, a count of the out-of-range DVHs, or a number (e.g., a percentage) relative to the total number of uncertainty DVHs, may be determined and presented on the DVH graph 900. For example, FIG. 9 illustrates that 28% of the uncertainty DVHs generated for the target structure are identified as out-of-range DVHs, 32% of the uncertainty DVHs generated for OAR-1 are identified as out-of-range DVHs, 15% of the uncertainty DVHs generated for OAR-2 are identified as out-of-range DVHs, and 4% of the uncertainty DVHs generated for OAR-3 are identified as out-of-range DVHs.

As illustrated in FIG. 9, for the target structure, the out-of-range DVHs and the corresponding out-of-range sub-band 914, as well as the extreme-scenario DVH 913, are below (or to the left of) the nominal DVH 811. This is because for the target structure, it is generally desirable that the target structure receive full radiation dose for an effective radiotherapy. Accordingly, any simulated scenarios with a lower radiation dose at the target structure (e.g., the extreme-scenario DVH 913 and those DVHs within the out-of-range sub-band 914) are deemed "failed DVHs". In contrast, for an OAR such as OAR-2, the out-of-range DVHs and the corresponding out-of-range sub-band 934, as well as the extreme-scenario DVH 933, are above (or to the right of) the nominal DVH 831. This is because for an OAR, it is desirable that the OAR receive less or no radiation dose to avoid irradiation. Accordingly, any simulated scenarios with a higher radiation dose at the OAR (e.g., the extreme-scenario DVH 933 and those DVHs within the out-of-range sub-band 934) are deemed "failed DVHs".

A robustness indicator of the treatment plan under evaluation may be generated using the identified out-of-range DVHs, or the out-of-range sub-band. In an example, the robustness indicator may be computed using a width of the out-of-range sub-band. A narrower sub-band indicates a higher robustness of the treatment plan. In an example, the robustness indicator may be represented by the out-of-range DVH percentage number. A smaller out-of-range DVH percentage number indicates a higher robustness of the treatment plan. In some examples, the robustness indicator may be computed using a combination (e.g., a weighted sum) of (1) the out-of-range sub-band width or the out-of-range DVH percentage number of the target structure, and (2) the out-of-range sub-band width or the out-of-range DVH percentage number of one or more OARs. The processor 114 may determine the treatment plan is robust if the robustness indicator satisfies a condition, such as falling below a threshold.

Figure 10:
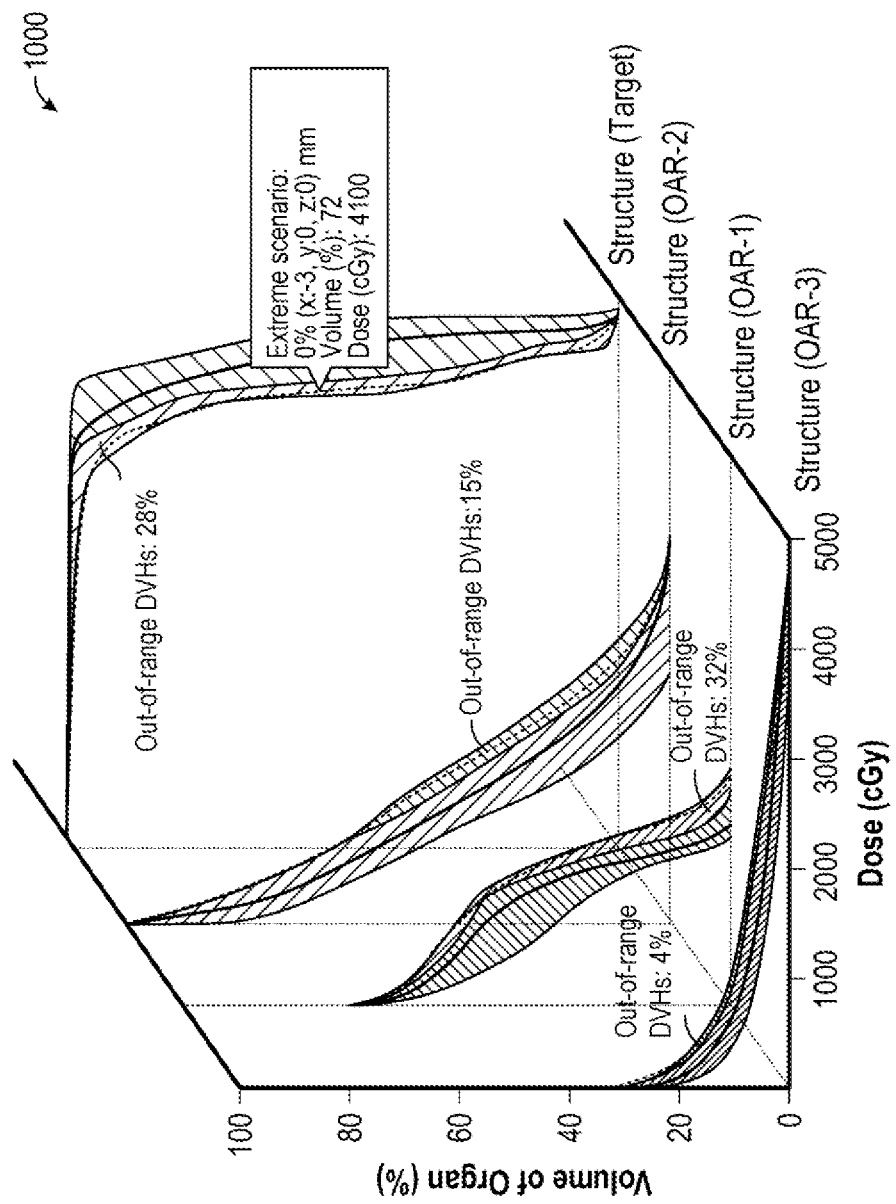
FIG. 10 is a diagram illustrating an example of a 3D DVH graph with user controlled display of dose distribution characteristics.

The DVH graph 900 may be displayed on a user interface, such as the display device 134 of the system 100. As discussed above with reference to FIG. 1, the user interface 136 may include one or more user controls (such as on-screen control elements, or a touch screen that enables finger touch and navigation control) that allow a user to manipulate the display of the DVH graph 900 to more effectively reveal the differences of the dose distribution characteristics between different structures. FIG. 10 illustrates an example of user controlled display of dose distribution characteristics on a 3D DVH graph 1000. In an example, via the user interface 136, a user may use a pointing device to position a cursor, or use a finger tap on a touch-screen, at a specific region of the 3D DVH graph (e.g., the DVH band, the extreme-scenario DVH, or the out-of-range DVH sub-band, etc.). In response, more information about the dose distribution characteristics may be automatically displayed, such as in a message box 1010. For example, as illustrated in FIG. 10, when a cursor hovers on the extreme-scenario DVH 913 of the target structure, the information about deviation scenarios and dose value received by a certain percentage of volume of the target structure may be displayed automatically. The display of information may update with cursor moving along the extreme-scenario DVH 913, or moving to a different region in the DVH characteristics of the target structure 910 (e.g., nominal DVH 811, the boundary DVHs 912A and 912B or the DVH band therebetween, or the out-of-range DVH sub-band 914), or moving to a region in the DVH characteristics of a different structure (e.g., 920 for OAR-1, 930 for OAR-2, and 940 for OAR-3).

Figure 11:
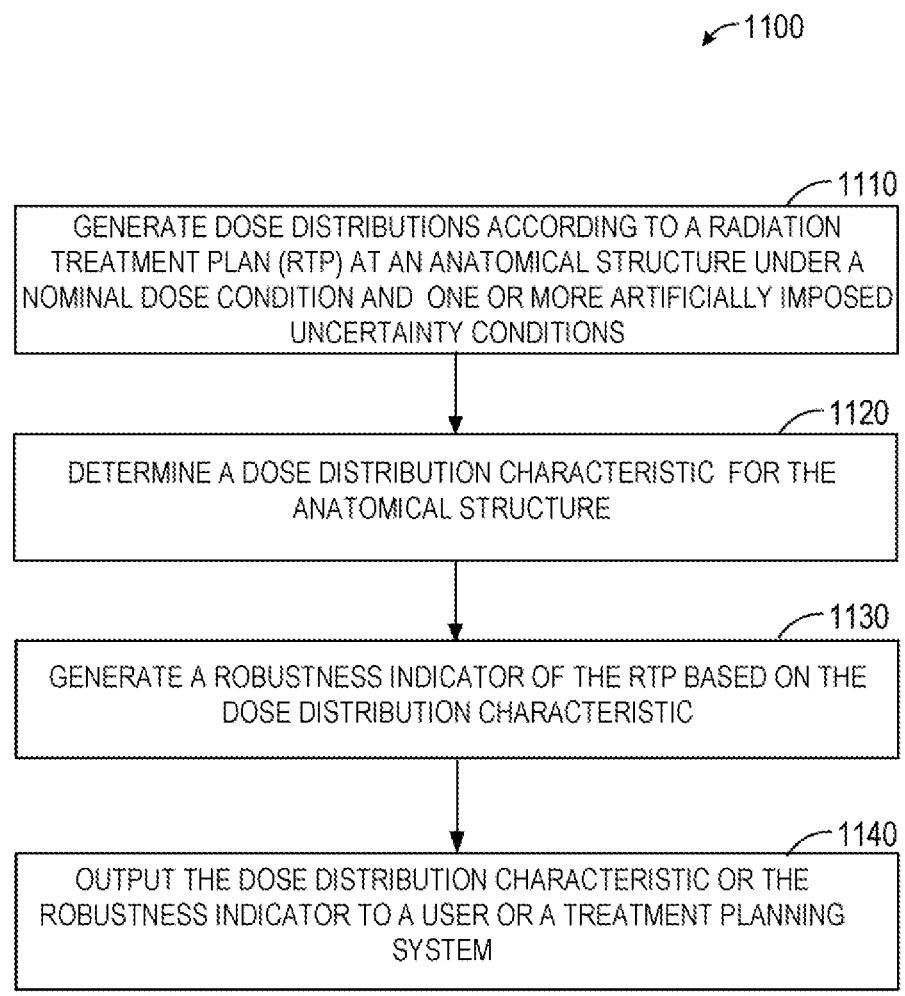
FIG. 11 is a flow chart illustrating an example of a method for evaluating robustness of a radiotherapy treatment plan.

FIG. 11 is a flow chart illustrating an exemplary method 1100 for evaluating robustness of a radiotherapy treatment plan for use in radiotherapy. A treatment plan needs to be robust to range uncertainties (e.g., systematic and random patient setup errors) to ensure the target volume receives a tumoricidal dose, and that the OAR doses are kept below complication thresholds. Robustness evaluation of a treatment plan against uncertainties can be helpful in a treatment planning process, and may influence clinical decision making. In an example, the method 1100 may be implemented in and executed by the radiotherapy system 100, which may include a radiation machine to provide radiotherapy to a subject according to a treatment plan. For example, at least a portion of the method 1100 may be machine-readable instructions executable by the processor 114.

Robustness of the treatment plan can be evaluated in a radiation simulation process comprising multiple simulated scenarios. At 1110, dose distributions may be generated at an anatomical structure under a nominal condition and one or more artificially imposed uncertainty conditions in accordance with the treatment plan under evaluation, such as by using the processor 114. The artificially imposed uncertainty conditions, which represent conditions deviating from the nominal conditions, may include range uncertainties, patient setup errors, or a combination thereof. Simulated scenarios corresponding to the uncertainty conditions are also referred to as deviation scenarios. In an example, the deviation scenarios may be simulated for a treatment under a systematic setup error represented by a certain deviation from a nominal position corresponding to the nominal condition, in one or more of +/−X, +/−Y, or +/−Z directions. In another example, scenarios may be simulated for a treatment under a certain percentage of Hounsfield Unit (HU) range uncertainty. In yet another example, the scenarios may be simulated for a treatment under a combination of a systematic setup error and a HU uncertainty.

An example of the dose distribution is a dose-volume histogram (DVH). DVHs may be calculated for different simulated scenarios at an anatomical structure, such as a nominal DVH under the nominal condition (i.e., free of artificially introduced error or uncertainty) and a number of uncertainty DVHs under respective artificially imposed uncertainty conditions.

In an example, multiple anatomical structures may be analyzed in a dose simulation to evaluate the robustness of the treatment plan. Examples of the anatomical structures may include a target structure to receive radiation treatment, and/or one or more structures at risk to avoid radiation treatment (e.g., one or more OARs). Accordingly, in some examples, a first DVH cluster (including a nominal DVH and one or more uncertainty DVHs) may be generated for the target structure, and additional one or more DVH clusters may be generated respectively for the one or more OARs, as discussed above with reference to FIG. 8.

At 1120, a dose distribution characteristic may be determined using the dose distributions, such as the DVHs, generated for the anatomical structure. The dose distribution characteristic may include one or more statistical features generated from the DVHs for different simulated scenarios. As discussed above with reference to FIG. 9, examples of the dose distribution characteristics generated from the DVHs for an anatomical structure may include boundary DVHs, a DVH range due to uncertainty conditions applied, a DVH band graphically representing the DVH range, an extreme-scenario DVH representing an uncertainty DVH that most significantly deviates from a dosimetric criterion (thus also referred to as the worst-scenario DVH), identification of out-of-range DVHs falling outside a tolerance margin with respect to a dosimetric criterion, an out-of-range sub-band graphically representing a range of the out-of-range DVHs, a count of the out-of-range DVHs, or a number (e.g., a percentage) relative to the total number of uncertainty DVHs, among others.

At 1130, a robustness indicator of the treatment plan under evaluation may be generated based on the dose distribution characteristics, such as one or more of the DVH characteristics. In an example, the robustness indicator can be computed using the DVH band width, a deviation of a boundary DVH from the nominal DVH, a deviation of the extreme-scenario DVH from the reference volume or the reference radiation dose, out-of-range sub-band width, or the out-of-range DVH percentage number, among others. In some instances, a composite robustness indicator may be generated using two or more different DVH characteristics as discussed herein. In some examples, the robustness indicator may be computed using a combination (e.g., a weighted sum) of the DVH characteristics of the target structure and the DVH characteristics of one or more OARs.

At 1140, the dose distribution characteristic (e.g., DVH characteristics of the target structure and one or more OARs) or the robustness indicator may be provided to a user or a treatment planning system (TPS). As illustrated in FIG. 9, the dose distribution characteristics of different structures may be stacked along the "structure" axis on the 3D Volume-Dose-Structure space. Spreading the DVH information along the structure axis can improve the visualization of differences among the dose distributions at different structures over different simulated scenarios, thereby improving the evaluation of treatment plan robustness. DVH characteristics such as the DVH band and the out-of-range DVH sub-band, among other characteristics, are graphical representation of statistics of the DVH curves, which can further ease the process of data interpretation and clinical decision making. In some examples, additional information about the dose distribution characteristics may be presented in a user interface, such as in a message box as shown in FIG. 10, upon receiving a user input from a user interface (e.g., the user interface 136).

The dose distribution characteristic or the robustness indicator may be provided to the therapy planning system. For example, if the dose distribution characteristic or the robustness indicator satisfies a specific robustness criterion indicating the treatment plan under evaluation is robust, then the treatment plan may be deployed in a radiotherapy treatment of the patient. However, if the treatment plan does not satisfy the specific robustness criterion, then the user may reject the treatment plan, or modify the treatment plan such as adding a treatment margin or changing an irradiation direction. In an example, a recommendation for accepting, rejecting, or modifying the treatment plan may be automatically generated and displayed on the display device 134, prompting the user for input.

Figure 12:
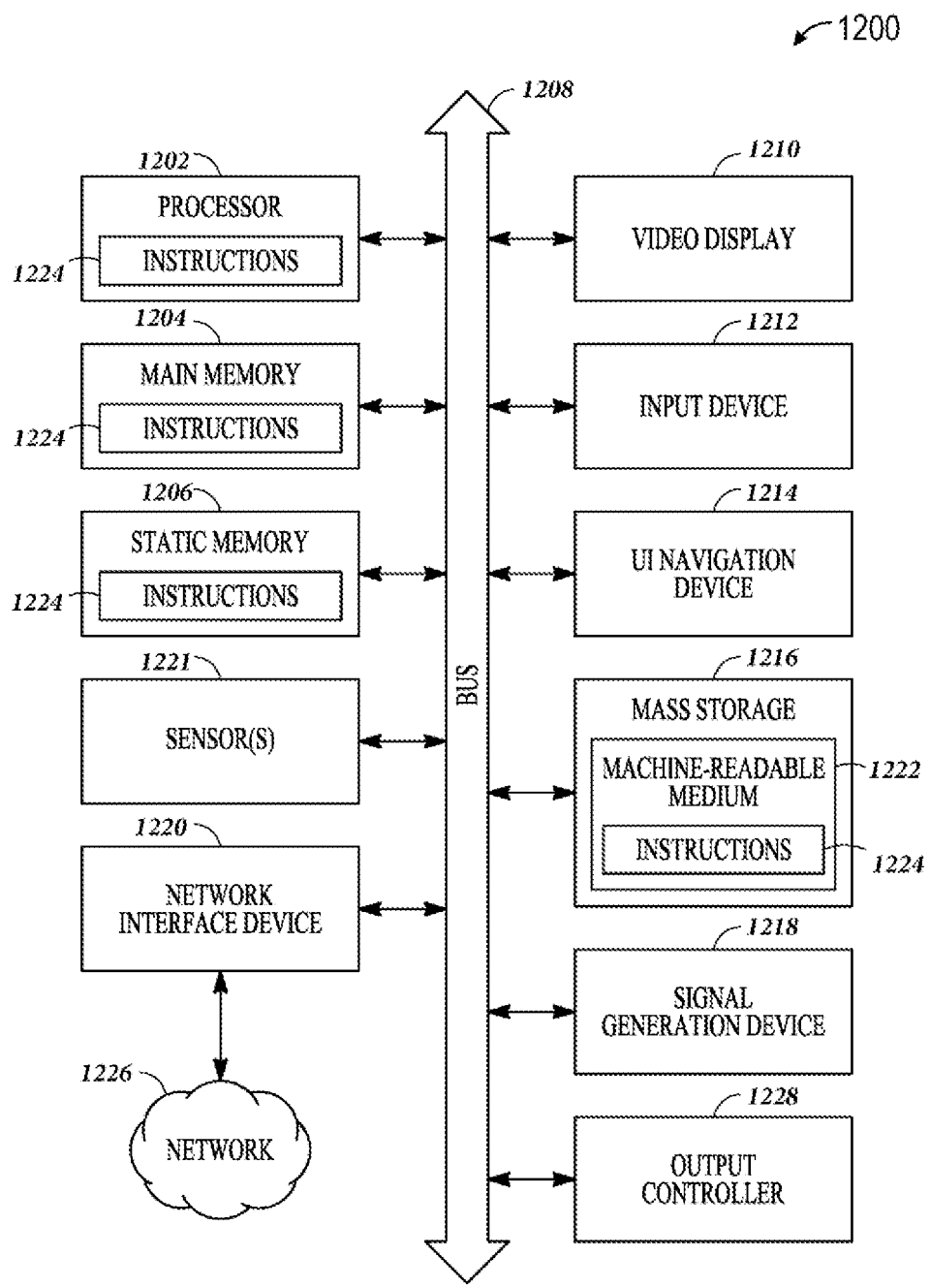
FIG. 12 illustrates generally a block diagram of an example machine upon which any one or more of the techniques (e.g., methodologies) discussed herein may perform.

FIG. 12 illustrates a block diagram of an example of a machine 1200 on which one or more of the methods as discussed herein can be implemented. In one or more examples, one or more items of the data processing device 112 can be implemented by the machine 1200. In alternative examples, the machine 1200 operates as a standalone device or may be connected (e.g., networked) to other machines. In one or more examples, the data processing device 112 may include one or more of the items of the machine 1200. In a networked deployment, the machine 1200 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1200 includes a processor 1202 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 1221 (e.g., a transducer that converts one form of energy (e.g., light, heat, electrical, mechanical, or other energy) to another form of energy), or the like, or a combination thereof), a main memory 1204 and a static memory 1206, which communicate with each other via a bus 1208. The machine 1200 (e.g., computer system) may further include a video display unit 1210 (e.g., a liquid crystal display (LCD) or a cathode ray tube (CRT)). The machine 1200 also includes an alphanumeric input device 1212 (e.g., a keyboard), a user interface (UI) navigation device 1214 (e.g., a mouse), a disk drive or mass storage unit 1216, a signal generation device 1218 (e.g., a speaker) and a network interface device 1220.

The disk drive unit 1216 includes a machine-readable medium 1222 on which is stored one or more sets of instructions and data structures (e.g., software) 1224 embodying or utilized by any one or more of the methodologies or functions described herein. The instructions 1224 may also reside, completely or at least partially, within the main memory 1204 and/or within the processor 1202 during execution thereof by the machine 1200, the main memory 1204 and the processor 1202 also constituting machine-readable media.

The machine 1200 as illustrated includes an output controller 1228. The output controller 1228 manages data flow to/from the machine 1200. The output controller 1228 is sometimes called a device controller, with software that directly interacts with the output controller 1228 being called a device driver.

While the machine-readable medium 1222 is shown in an example to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 1224 may further be transmitted or received over a communications network 1226 using a transmission medium. The instructions 1224 may be transmitted using the network interface device 1220 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

Example 1 is a system for evaluating robustness of a radiotherapy treatment plan used by a radiation therapy device to treat a patient. The system comprises a processor configured to generate, in a radiation simulation in accordance with the radiotherapy treatment plan, dose distributions at an anatomical structure under a nominal condition and one or more artificially imposed uncertainty conditions, to determine a dose distribution characteristic for the anatomical structure using the dose distributions, and to generate a robustness indicator of the radiotherapy treatment plan based on the dose distribution characteristic. The system comprises a memory configured store the dose distribution characteristic or the robustness indicator accessible by a user or a treatment planning system.

In Example 2, the subject matter of Example 1 optionally includes the anatomical structure that can include a target structure to receive radiation treatment and at least one structure at risk to avoid radiation treatment. The processor can be configured to determine a first dose distribution characteristic using first dose distributions at the target structure, and a second dose distribution characteristic using second dose distributions at the at least one structure at risk, and generate a three-dimensional (3D) graphical representation of the first and second dose distribution characteristics in a dose-volume-structure space to be displayed on a display.

In Example 3, the subject matter of any one or more of Examples 1-2 optionally includes the dose distributions that can include dose-volume histograms (DVHs) each representing tissue volumes of the anatomical structure receiving respective radiation doses, the DVHs including: a nominal DVH corresponding to the nominal condition; and one or more uncertainty DVHs corresponding to the one or more artificially imposed uncertainty conditions using the dose distributions.

In Example 4, the subject matter of Example 3 optionally includes the dose distribution characteristic that can include (1) a first boundary DVH corresponding to a lowest dose across a range of volumes of the anatomical structure and (2) a second boundary DVH corresponding to a highest dose across the range of volumes of the anatomical structure, the first and second boundary DVHs defining a DVH range. The processor circuit can be configured to generate a DVH band graphically representing the DVH range to be displayed on a display.

In Example 5, the subject matter of Example 4 optionally includes the processor that can be configured to generate the robustness indicator of the radiotherapy treatment plan based on at least one of: a first deviation of the first boundary DVH from the nominal DVH; a second deviation of the second boundary DVH from the nominal DVH; or a third deviation of the second boundary DVH from the first boundary DVH.

In Example 6, the subject matter of any one or more of Examples 3-5 optionally includes the processor that can be configured to determine the dose distribution characteristic including identifying, from the one or more uncertainty DVHs, an extreme-scenario DVH based on a dosimetric criterion including at least one of a reference tissue volume or a reference radiation dose, and to generate a graphical representation of the extreme-scenario DVH to be displayed on a display.

In Example 7, the subject matter of Example 6 optionally includes the processor that can be configured to generate the robustness indicator of the radiotherapy treatment plan based on a deviation of the extreme-scenario DVH from the dosimetric criterion.

In Example 8, the subject matter of any one or more of Examples 6-7 optionally includes the processor that can be configured to: generate, for a target structure to receive radiation treatment, a first set of DVHs including a first nominal DVH corresponding to the nominal condition and first one or more uncertainty DVHs corresponding to the one or more artificially imposed uncertainty conditions; and identify, from the first set of DVHs, a first extreme-scenario DVH that has at least one of (1) a minimum radiation dose received by a first reference tissue volume of the target structure, or (2) a minimum tissue volume of the target structure receiving a first reference radiation dose.

In Example 9, the subject matter of any one or more of Examples 6-8 optionally includes the processor that can be configured to: generate, for a structure at risk to avoid radiation treatment, a second set of DVHs including a second nominal DVH corresponding to the nominal condition and second one or more uncertainty DVHs corresponding to the one or more artificially imposed uncertainty conditions; and identify, from the second uncertainty DVHs, a second extreme-scenario DVH that has at least one of (1) a maximum radiation dose received by a second reference tissue volume of the structure at risk, or (2) a maximum tissue volume of the structure at risk receiving a second reference radiation dose.

In Example 10, the subject matter of any one or more of Examples 3-9 optionally includes the processor that can be configured to determine the dose distribution characteristic including identifying, from the one or more uncertainty DVHs, one or more out-of-range DVHs falling outside a tolerance margin based on a dosimetric criterion including at least one of a reference tissue volume or a reference radiation dose, and to generate an out-of-range DVH sub-band graphically representing the identified one or more out-of-range DVHs to be displayed on a display.

In Example 11, the subject matter of Example 10 optionally includes the processor that can be configured to generate the robustness indicator of the radiotherapy treatment plan using a count of the out-of-range DVHs relative to a count of the one or more uncertainty DVHs.

In Example 12, the subject matter of any one or more of Examples 10-11 optionally includes the processor that can be configured to: generate, for a target structure to receive radiation treatment, a first set of DVHs including a first nominal DVH corresponding to the nominal condition and first one or more uncertainty DVHs corresponding to the one or more artificially imposed uncertainty conditions; and identify, from the first uncertainty DVHs, one or more out-of-range DVHs each having a lower radiation dose at a reference tissue volume than a first reference radiation dose by a first tolerance margin.

In Example 13, the subject matter of any one or more of Examples 10-12 optionally includes the processor that can be configured to: generate, for a structure at risk to avoid radiation treatment, a second set of DVHs including a second nominal DVH corresponding to the nominal condition and second one or more uncertainty DVHs corresponding to the one or more artificially imposed uncertainty conditions; and identify, from the second uncertainty DVHs, one or more out-of-range DVHs each having a higher radiation dose at a reference tissue volume than a second reference radiation dose by a second tolerance margin.

In Example 14, the subject matter of any one or more of Examples 1-13 optionally includes the radiotherapy that can include a proton therapy, and wherein the dose distributions are determined for an anatomical structure under a nominal condition and one or more artificially imposed uncertainty conditions in a simulated proton therapy.

In Example 15, the subject matter of Example 14 optionally includes the one or more artificially imposed uncertainty conditions that can include deviations from the nominal condition representing one or more of range uncertainties associated with a proton beam or patient setup errors.

In Example 16, the subject matter of any one or more of Examples 1-15 optionally includes the processor that can be further configured to modify, or generate a recommendation to modify, the radiotherapy treatment plan based on the robustness indicator of the radiotherapy treatment plan.

Example 17 is a method for evaluating robustness of a radiotherapy treatment plan used by a radiation therapy device to treat a patient. The method comprises steps of: generating, via a processor, dose distributions at an anatomical structure under a nominal condition and one or more artificially imposed uncertainty conditions using the radiotherapy treatment plan; determining a dose distribution characteristic for the anatomical structure using the dose distributions; generating a robustness indicator of the radiotherapy treatment plan based on the dose distribution characteristic; and providing the dose distribution characteristic or the robustness indicator to a user or a treatment planning system.

In Example 18, the subject matter of Example 17 optionally includes the anatomical structure that can include a target structure to receive radiation treatment and at least one structure at risk to avoid radiation treatment. The method comprises steps of: determining a first dose distribution characteristic using first dose distributions at the target structure, and a second dose distribution characteristic using second dose distributions at the at least one structure at risk; and generating a three-dimensional (3D) graphical representation of the first and second dose distribution characteristics in a dose-volume-structure space.

In Example 19, the subject matter of any one or more of Examples 17-18 optionally includes the dose distributions that an include dose-volume histograms (DVHs) each representing tissue volumes of the anatomical structure receiving respective radiation doses. The DVHs can include: a nominal DVH corresponding to the nominal condition; and one or more uncertainty DVHs corresponding to the one or more artificially imposed uncertainty conditions using the dose distributions.

In Example 20, the subject matter of Example 19 optionally includes the dose distribution characteristic that can include (1) a first boundary DVH corresponding to a lowest dose across a range of volumes of the anatomical structure and (2) a second boundary DVH corresponding to a highest dose across the range of volumes of the anatomical structure, wherein: generating the robustness indicator of the radiotherapy treatment plan is based on a DVH range defined by the first and second boundary DVHs; and providing the dose distribution characteristic or the robustness indicator includes displaying a DVH band graphically representing the DVH range.

In Example 21, the subject matter of any one or more of Examples 19-20 optionally includes steps of: identifying, from the one or more uncertainty DVHs, an extreme-scenario DVH satisfying a dosimetric criterion with respect to the nominal DVH; and generating the robustness indicator of the radiotherapy treatment plan based on a deviation of the extreme-scenario DVH from the nominal DVH; and wherein providing the dose distribution characteristic or the robustness indicator includes displaying a graphical representation of the extreme-scenario DVH.

In Example 22, the subject matter of any one or more of Examples 19-21 optionally includes steps of: identifying, from the one or more uncertainty DVHs, one or more out-of-range DVHs falling outside a tolerance margin with respect to the nominal DVH; and generating the robustness indicator of the radiotherapy treatment plan based on a count of the out-of-range DVHs relative to a count of the one or more uncertainty DVHs; and wherein providing the dose distribution characteristic or the robustness indicator includes displaying an out-of-range DVH sub-band graphically representing the identified one or more out-of-range DVHs.

In Example 23, the subject matter of any one or more of Examples 17-22 optionally includes modifying, or generating a recommendation to modify, the radiotherapy treatment plan based on the robustness indicator of the radiotherapy treatment plan.

In Example 24, the subject matter of any one or more of Examples 17-23 optionally includes the radiotherapy that can include a proton therapy, and wherein the one or more artificially imposed uncertainty conditions can include deviations from the nominal condition representing one or more of range uncertainties associated with a proton beam or patient setup errors.

Additional Notes

The above detailed description includes references to the accompanying drawings, which form a part of the detailed description. The drawings show, by way of illustration but not by way of limitation, specific examples in which the disclosure can be practiced. These examples are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the examples thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended aspects, the terms "including" and "in which" are used as the plain-English equivalents of the respective terms "comprising" and "wherein." Also, in the following aspects, the terms "comprising," "including," and "having" are intended to be open-ended to mean that there may be additional elements other than the listed elements, such that after such a term (e.g., comprising, including, having) in a aspect are still deemed to fall within the scope of that aspect. Moreover, in the following aspects, the terms "first," "second," and "third," and so forth, are used merely as labels, and are not intended to impose numerical requirements on their objects.

Examples of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other examples of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples may include a computer-readable medium or machine-readable medium encoded with instructions operable to configure an electronic device to perform methods as described in the above examples. An implementation of such methods may include software code, such as microcode, assembly language code, a higher-level language code, or the like (e.g., "source code"). Such software code may include computer readable instructions for performing various methods (e.g., "object" or "executable code"). The software code may form portions of computer program products. Software implementations of the examples described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an example, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various examples of the disclosure, the method of creating a component or module can be implemented in software, hardware, or a combination thereof. The methods provided by various examples of the present disclosure, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved, and other advantageous results attained. Having described aspects of the disclosure in detail, it will be apparent that modifications and variations are possible without departing from the scope of aspects of the disclosure as defined in the appended aspects. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary examples. Many other examples will be apparent to those of skill in the art upon reviewing the above description. The scope of the disclosure should, therefore, be determined with reference to the appended aspects, along with the full scope of equivalents to which such aspects are entitled.

Also, in the above Detailed Description, various features may be grouped together to streamline the disclosure. This should not be interpreted as intending that an unexpected disclosed feature is essential to any aspect. Rather, inventive subject matter may lie in less than all features of a particular disclosed example. Thus, the following aspects are hereby incorporated into the Detailed Description, with each aspect standing on its own as a separate example. The scope of the disclosure should be determined with reference to the appended aspects, along with the full scope of equivalents to which such aspects are entitled. Further, the limitations of the following aspects are not written in means-plus-function format and are not intended to be interpreted based on 35 U.S.C. § 112, sixth paragraph, unless and until such aspect limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the aspects.

What is claimed is:

1. A system for evaluating robustness of a radiotherapy treatment plan used by a radiation therapy device to treat a patient, the system comprising:
   a processor configured to:
      generate, in a radiation simulation in accordance with the radiotherapy treatment plan, dose distributions at an anatomical structure under a nominal condition and one or more artificially imposed uncertainty conditions;
      determine a dose distribution characteristic for the anatomical structure using the dose distributions; and
      generate a robustness indicator of the radiotherapy treatment plan based on the dose distribution characteristic; and
   a memory configured store the dose distribution characteristic or the robustness indicator accessible by a user or a treatment planning system.

2. The system of claim 1, wherein the anatomical structure includes a target structure to receive radiation treatment and at least one structure at risk to avoid radiation treatment, and wherein the processor is configured to:
   determine a first dose distribution characteristic using first dose distributions at the target structure, and a second dose distribution characteristic using second dose distributions at the at least one structure at risk; and
   generate a three-dimensional (3D) graphical representation of the first and second dose distribution characteristics in a dose-volume-structure space to be displayed on a display.

3. The system of claim 1, wherein the dose distributions include dose-volume histograms (DVHs) each representing tissue volumes of the anatomical structure receiving respective radiation doses, the DVHs including:
   a nominal DVH corresponding to the nominal condition; and
   one or more uncertainty DVHs corresponding to the one or more artificially imposed uncertainty conditions using the dose distributions.

4. The system of claim 3, wherein the dose distribution characteristic includes (1) a first boundary DVH corresponding to a lowest dose across a range of volumes of the anatomical structure and (2) a second boundary DVH corresponding to a highest dose across the range of volumes of the anatomical structure, the first and second boundary DVHs defining a DVH range; and
   wherein the processor circuit is configured to generate a DVH band graphically representing the DVH range to be displayed on a display.

5. The system of claim 4, wherein the processor is configured to generate the robustness indicator of the radiotherapy treatment plan based on at least one of:
   a first deviation of the first boundary DVH from the nominal DVH;
   a second deviation of the second boundary DVH from the nominal DVH; or
   a third deviation of the second boundary DVH from the first boundary DVH.

6. The system of claim 3, wherein the processor is configured to:
   determine the dose distribution characteristic including identifying, from the one or more uncertainty DVHs, an extreme-scenario DVH based on a dosimetric criterion including at least one of a reference tissue volume or a reference radiation dose; and
   generate a graphical representation of the extreme-scenario DVH to be displayed on a display.

7. The system of claim 6, wherein the processor is configured to generate the robustness indicator of the radiotherapy treatment plan based on a deviation of the extreme-scenario DVH from the dosimetric criterion.

8. The system of claim 6, wherein the processor is configured to:
   generate, for a target structure to receive radiation treatment, a first set of DVHs including a first nominal DVH corresponding to the nominal condition and first one or more uncertainty DVHs corresponding to the one or more artificially imposed uncertainty conditions; and
   identify, from the first set of DVHs, a first extreme-scenario DVH that has at least one of (1) a minimum radiation dose received by a first reference tissue volume of the target structure, or (2) a minimum tissue volume of the target structure receiving a first reference radiation dose.

9. The system of claim 6, wherein the processor is configured to:
   generate, for a structure at risk to avoid radiation treatment, a second set of DVHs including a second nominal DVH corresponding to the nominal condition and second one or more uncertainty DVHs corresponding to the one or more artificially imposed uncertainty conditions; and
   identify, from the second uncertainty DVHs, a second extreme-scenario DVH that has at least one of (1) a maximum radiation dose received by a second reference tissue volume of the structure at risk, or (2) a maximum tissue volume of the structure at risk receiving a second reference radiation dose.

10. The system of claim 3, wherein the processor is configured to:
    determine the dose distribution characteristic including identifying, from the one or more uncertainty DVHs, one or more out-of-range DVHs falling outside a tolerance margin based on a dosimetric criterion including at least one of a reference tissue volume or a reference radiation dose; and
    generate an out-of-range DVH sub-band graphically representing the identified one or more out-of-range DVHs to be displayed on a display.

11. The system of claim 10, wherein the processor is configured to generate the robustness indicator of the radiotherapy treatment plan using a count of the out-of-range DVHs relative to a count of the one or more uncertainty DVHs.

12. The system of claim 10, wherein the processor is configured to:
    generate, for a target structure to receive radiation treatment, a first set of DVHs including a first nominal DVH corresponding to the nominal condition and first one or more uncertainty DVHs corresponding to the one or more artificially imposed uncertainty conditions; and identify, from the first uncertainty DVHs, one or more out-of-range DVHs each having a lower radiation dose at a reference tissue volume than a first reference radiation dose by a first tolerance margin.

13. The system of claim 10, wherein the processor is configured to:

generate, for a structure at risk to avoid radiation treatment, a second set of DVHs including a second nominal DVH corresponding to the nominal condition and second one or more uncertainty DVHs corresponding to the one or more artificially imposed uncertainty conditions; and identify, from the second uncertainty DVHs, one or more out-of-range DVHs each having a higher radiation dose at a reference tissue volume than a second reference radiation dose by a second tolerance margin.

14. The system of claim 1, wherein the radiotherapy includes a proton therapy, and wherein the dose distributions are determined for an anatomical structure under a nominal condition and one or more artificially imposed uncertainty conditions in a simulated proton therapy.

15. The system of claim 14, wherein the one or more artificially imposed uncertainty conditions include deviations from the nominal condition representing one or more of range uncertainties associated with a proton beam or patient setup errors.

16. The system of claim 1, wherein the processor is further configured to modify, or generate a recommendation to modify, the radiotherapy treatment plan based on the robustness indicator of the radiotherapy treatment plan.

17. A method for evaluating robustness of a radiotherapy treatment plan used by a radiation therapy device to treat a patient, the method comprising:

generating, via a processor, dose distributions at an anatomical structure under a nominal condition and one or more artificially imposed uncertainty conditions using the radiotherapy treatment plan;

determining a dose distribution characteristic for the anatomical structure using the dose distributions;

generating a robustness indicator of the radiotherapy treatment plan based on the dose distribution characteristic; and providing the dose distribution characteristic or the robustness indicator to a user or a treatment planning system.

18. The method of claim 17, wherein the anatomical structure includes a target structure to receive radiation treatment and at least one structure at risk to avoid radiation treatment, the method comprising:

determining a first dose distribution characteristic using first dose distributions at the target structure, and a second dose distribution characteristic using second dose distributions at the at least one structure at risk; and generating a three-dimensional (3D) graphical representation of the first and second dose distribution characteristics in a dose-volume-structure space.

19. The method of claim 17, wherein the dose distributions include dose-volume histograms (DVHs) each representing tissue volumes of the anatomical structure receiving respective radiation doses, the DVHs including:

a nominal DVH corresponding to the nominal condition; and one or more uncertainty DVHs corresponding to the one or more artificially imposed uncertainty conditions using the dose distributions.

20. The method of claim 19, wherein the dose distribution characteristic includes (1) a first boundary DVH corresponding to a lowest dose across a range of volumes of the anatomical structure and (2) a second boundary DVH corresponding to a highest dose across the range of volumes of the anatomical structure, wherein:

generating the robustness indicator of the radiotherapy treatment plan is based on a DVH range defined by the first and second boundary DVHs; and providing the dose distribution characteristic or the robustness indicator includes displaying a DVH band graphically representing the DVH range.

21. The method of claim 19, comprising:

identifying, from the one or more uncertainty DVHs, an extreme-scenario DVH satisfying a dosimetric criterion with respect to the nominal DVH; and generating the robustness indicator of the radiotherapy treatment plan based on a deviation of the extreme-scenario DVH from the nominal DVH;

wherein providing the dose distribution characteristic or the robustness indicator includes displaying a graphical representation of the extreme-scenario DVH.

22. The method of claim 19, comprising:

identifying, from the one or more uncertainty DVHs, one or more out-of-range DVHs falling outside a tolerance margin with respect to the nominal DVH; and generating the robustness indicator of the radiotherapy treatment plan based on a count of the out-of-range DVHs relative to a count of the one or more uncertainty DVHs;

wherein providing the dose distribution characteristic or the robustness indicator includes displaying an out-of-range DVH sub-band graphically representing the identified one or more out-of-range DVHs.

23. The method of claim 17, comprising modifying, or generating a recommendation to modify, the radiotherapy treatment plan based on the robustness indicator of the radiotherapy treatment plan.

24. The method of claim 17, wherein the radiotherapy includes a proton therapy, and wherein the one or more artificially imposed uncertainty conditions include deviations from the nominal condition representing one or more of range uncertainties associated with a proton beam or patient setup errors.

* * * * *